US012691228B2

(12) United States Patent
Besson et al.

(10) Patent No.:      US 12,691,228 B2
(45) Date of Patent:           Jul. 28, 2026

(54) AUTO-INJECTOR WITH NEEDLE COVER

(71) Applicant: Becton Dickinson France, Le Pont-de-Claix (FR)

(72) Inventors: Nicolas Besson, Treffort (FR); Adrien Plouvier, Saint Martin D'Heres (FR)

(73) Assignee: Becton Dickinson France, Le Pont de Claix (FR)

( * ) Notice: Subject to any disclaimer, the term of this patent is extended or adjusted under 35 U.S.C. 154(b) by 1002 days.

(21) Appl. No.: 17/425,967

(22) PCT Filed: Feb. 26, 2020

(86) PCT No.: PCT/EP2020/055003
§ 371 (c)(1),
(2) Date: Jul. 27, 2021

(87) PCT Pub. No.: WO2020/173991
PCT Pub. Date: Sep. 3, 2020

(65) Prior Publication Data
US 2022/0111152 A1      Apr. 14, 2022

(30) Foreign Application Priority Data

Feb. 26, 2019    (EP) ..................................... 19305226

(51) Int. Cl.
A61M 5/315          (2006.01)
A61M 5/20           (2006.01)
A61M 5/32           (2006.01)

(52) U.S. Cl.
CPC .......... A61M 5/31571 (2013.01); A61M 5/20 (2013.01); A61M 5/31501 (2013.01);
(Continued)

(58) Field of Classification Search
CPC .. A61M 2005/2006; A61M 2005/2013; A61M 2005/206; A61M 2005/2073;
(Continued)

(56) References Cited

U.S. PATENT DOCUMENTS 3,562,564 A      2/1971   Potter
6,056,728 A      5/2000   Von Schuckmann
(Continued)

FOREIGN PATENT DOCUMENTS

CN          102112168 B      5/2013
CN          103249617 A      8/2013
(Continued)

*Primary Examiner* — Shefali D Patel
(74) *Attorney, Agent, or Firm* — The Webb Law Firm

(57)          ABSTRACT

A drug delivery device includes a housing, a syringe assembly comprising a barrel, a stopper, and a cannula, with at least a portion of the syringe assembly positioned within the housing, a drive assembly configured to move the stopper within the barrel upon actuation of the drive assembly, with at least a portion of the drive assembly positioned within the housing, a lever actuation member moveable between a locked position where the actuation of the drive assembly is prevented and a released position where the actuation of the drive assembly is allowed, and a needle cover having a pre-use position where the cannula is positioned within the needle cover, an actuation position where the needle cover is configured to actuate the drive assembly, and a post-use position where the cannula is positioned within the needle cover. The needle cover is configured to engage the lever actuation member and move the lever actuation member to the released position when the needle cover is in the actuation position.

13 Claims, 31 Drawing Sheets

(52) U.S. Cl.
CPC ........ *A61M 5/3205* (2013.01); *A61M 5/3243* (2013.01); *A61M 5/3257* (2013.01); *A61M 2005/2013* (2013.01); *A61M 2005/206* (2013.01); *A61M 2005/2073* (2013.01); *A61M 2005/208* (2013.01)

(58) Field of Classification Search
CPC .... A61M 2005/208; A61M 2005/2403; A61M 2005/2485; A61M 5/20; A61M 5/2033; A61M 5/24; A61M 5/2422; A61M 5/315; A61M 5/31501; A61M 5/31511; A61M 5/31565; A61M 5/31571; A61M 5/31576; A61M 5/32; A61M 5/3202; A61M 5/3204; A61M 5/3205; A61M 5/321; A61M 5/3243; A61M 5/3245; A61M 5/3257
See application file for complete search history.

(56) References Cited

U.S. PATENT DOCUMENTS

| | | | |
|---|---|---|---|
| 6,090,070 | A | 7/2000 | Hager et al. |
| 6,183,446 | B1 | 2/2001 | Jeanbourquin |
| 6,746,429 | B2 | 6/2004 | Sadowski et al. |
| 7,112,187 | B2 | 9/2006 | Karlsson |
| 7,357,790 | B2 | 4/2008 | Hommann et al. |
| 7,442,185 | B2 | 10/2008 | Amark et al. |
| 7,563,252 | B2 | 7/2009 | Marshall et al. |
| 7,717,877 | B2 | 5/2010 | Lavi et al. |
| 7,879,007 | B2 | 2/2011 | Hommann |
| 7,988,675 | B2 | 8/2011 | Gillespie, III et al. |
| 8,021,335 | B2 | 9/2011 | Lesch, Jr. |
| 8,038,649 | B2 | 10/2011 | Kronestedt |
| 8,062,255 | B2 | 11/2011 | Brunnberg et al. |
| 8,172,797 | B2 | 5/2012 | Hogdahl |
| 8,177,745 | B2 | 5/2012 | Brechbuehler et al. |
| 8,317,751 | B2 | 11/2012 | Habeshaw et al. |
| 8,337,472 | B2 | 12/2012 | Edginton et al. |
| 8,376,998 | B2 | 2/2013 | Daily et al. |
| 8,409,149 | B2 | 4/2013 | Hommann et al. |
| 8,496,619 | B2 | 7/2013 | Kramer et al. |
| 8,579,866 | B2 | 11/2013 | Morgan et al. |
| 8,679,061 | B2 | 3/2014 | Julian et al. |
| 8,715,246 | B2 | 5/2014 | Giambattista et al. |
| 8,747,357 | B2 | 6/2014 | Stamp et al. |
| 8,758,301 | B2 | 6/2014 | Shang et al. |
| 8,915,882 | B2 | 12/2014 | Cabiri |
| 8,932,254 | B2 | 1/2015 | Eaton |
| 8,945,049 | B2 | 2/2015 | Hommann et al. |
| 8,956,331 | B2 | 2/2015 | Johansen et al. |
| 8,968,236 | B2 | 3/2015 | Jennings et al. |
| 8,992,477 | B2 | 3/2015 | Raday et al. |
| 8,998,855 | B2 | 4/2015 | Hudson et al. |
| 9,011,375 | B2 | 4/2015 | Holmqvist et al. |
| 9,033,932 | B2 | 5/2015 | Holmqvist |
| 9,072,833 | B2 | 7/2015 | Jennings et al. |
| 9,078,978 | B2 | 7/2015 | Schraga |
| 9,084,849 | B2 | 7/2015 | Edwards et al. |
| 9,125,988 | B2 | 9/2015 | Karlsson |
| 9,180,256 | B2 | 11/2015 | Eaton |
| 9,180,259 | B2 | 11/2015 | Lesch, Jr. |
| 9,186,462 | B2 | 11/2015 | Lanzi et al. |
| 9,199,038 | B2 | 12/2015 | Daniel |
| 9,199,041 | B2 | 12/2015 | Edginton |
| 9,205,199 | B2 | 12/2015 | Kemp et al. |
| 9,216,251 | B2 | 12/2015 | Daniel |
| 9,233,213 | B2 | 1/2016 | Olson et al. |
| 9,259,536 | B2 | 2/2016 | Gillespie, III et al. |
| 9,302,047 | B2 | 4/2016 | Alexandersson |
| 9,327,084 | B2 | 5/2016 | Evans |
| 9,352,099 | B2 | 5/2016 | Roberts et al. |
| 9,358,345 | B2 | 6/2016 | Brereton et al. |
| 9,364,610 | B2 | 6/2016 | KraMer et al. |
| 9,364,611 | B2 | 6/2016 | KraMer et al. |
| 9,427,528 | B2 | 8/2016 | Hommann et al. |
| 9,427,531 | B2 | 8/2016 | Hourmand et al. |
| 9,446,195 | B2 | 9/2016 | Kramer et al. |
| 9,486,583 | B2 | 11/2016 | Lannan et al. |
| 9,522,233 | B2 | 12/2016 | Bicknell et al. |
| 9,526,837 | B2 | 12/2016 | Carrel et al. |
| 9,533,099 | B2 | 1/2017 | Maritan |
| 9,533,102 | B2 | 1/2017 | Lesch, Jr. |
| 9,586,011 | B2 | 3/2017 | Roberts et al. |
| 9,604,011 | B2 | 3/2017 | Roberts et al. |
| 9,616,181 | B2 | 4/2017 | Kemp et al. |
| 9,629,959 | B2 | 4/2017 | Lesch |
| 9,724,480 | B2 | 8/2017 | Harms et al. |
| 9,744,306 | B2 | 8/2017 | Cowe |
| 9,764,092 | B2 | 9/2017 | Cabiri |
| 9,764,101 | B2 | 9/2017 | McLoughlin et al. |
| 9,775,948 | B2 | 10/2017 | Bechmann et al. |
| 9,789,257 | B2 | 10/2017 | Travanty |
| 9,833,579 | B2 | 12/2017 | Pedersen et al. |
| 9,855,392 | B2 | 1/2018 | Hommann et al. |
| 9,867,942 | B2 | 1/2018 | Alexandersson |
| 9,867,949 | B2 | 1/2018 | Sund et al. |
| 9,872,961 | B2 | 1/2018 | Fourt et al. |
| 9,901,674 | B2 | 2/2018 | McLoughlin et al. |
| 9,913,943 | B2 | 3/2018 | Fourt et al. |
| 9,925,342 | B2 | 3/2018 | Carrel et al. |
| RE46,789 | E | 4/2018 | Olson |
| 9,950,125 | B2 | 4/2018 | Wotton et al. |
| 9,956,353 | B2 | 5/2018 | Rao et al. |
| 9,974,904 | B2 | 5/2018 | Burk et al. |
| 9,981,084 | B2 | 5/2018 | Kadamus et al. |
| 9,987,436 | B2 | 6/2018 | Giambattista et al. |
| 9,999,734 | B2 | 6/2018 | Cowe |
| 10,004,852 | B2 | 6/2018 | Marsh et al. |
| 10,046,115 | B2 | 8/2018 | Bokelman et al. |
| 10,080,847 | B2 | 9/2018 | Roberts et al. |
| 10,086,145 | B2 | 10/2018 | Cabiri et al. |
| 10,086,152 | B2 | 10/2018 | Imai et al. |
| 10,092,073 | B2 | 10/2018 | Wagoner |
| 10,092,698 | B2 | 10/2018 | Park et al. |
| 10,092,703 | B2 | 10/2018 | Mounce et al. |
| 10,105,496 | B2 | 10/2018 | Aneas |
| 10,118,001 | B2 | 11/2018 | Fourt et al. |
| 10,130,774 | B2 | 11/2018 | Daniel |
| 10,137,255 | B2 | 11/2018 | Kemp |
| 10,137,256 | B2 | 11/2018 | Taal et al. |
| 10,149,939 | B2 | 12/2018 | Giambattista et al. |
| 10,159,791 | B2 | 12/2018 | Guillermo |
| 10,159,800 | B2 | 12/2018 | Säll |
| 10,183,121 | B2 | 1/2019 | Cowe |
| 10,252,005 | B2 | 4/2019 | Row et al. |
| 10,272,210 | B2 | 4/2019 | Keitel |
| 10,300,218 | B2 | 5/2019 | Stefanov |
| 10,307,545 | B2 | 6/2019 | Maxfield |
| 10,322,237 | B2 | 6/2019 | Fabien |
| 10,335,553 | B2 | 7/2019 | Bendek |
| 10,350,356 | B2 | 7/2019 | Hirschel et al. |
| 10,363,377 | B2 | 7/2019 | Atterbury et al. |
| 10,363,378 | B2 | 7/2019 | Moore |
| 10,376,641 | B2 | 8/2019 | Hirschel et al. |
| 10,384,009 | B2 | 8/2019 | Olson et al. |
| 10,406,294 | B2 | 9/2019 | Ward et al. |
| 10,417,937 | B2 | 9/2019 | Gaillot et al. |
| 10,485,934 | B2 | 11/2019 | Bostrom |
| 10,493,212 | B2 | 12/2019 | Tschirren et al. |
| 10,493,213 | B2 | 12/2019 | Hommann et al. |
| 10,500,337 | B2 | 12/2019 | Fabien et al. |
| 10,525,201 | B2 | 1/2020 | Brunnberg et al. |
| 10,561,798 | B2 | 2/2020 | Holland et al. |
| 10,643,744 | B2 | 5/2020 | Hopper et al. |
| 10,646,643 | B2 | 5/2020 | Cabiri et al. |
| 10,758,683 | B2 | 9/2020 | Gibson et al. |
| 10,799,647 | B2 | 10/2020 | Hostettler et al. |
| 10,821,072 | B2 | 11/2020 | Wotton et al. |
| 10,881,799 | B2 | 1/2021 | Hirschel et al. |
| 10,888,668 | B2 | 1/2021 | Mosebach et al. |
| 10,894,127 | B2 | 1/2021 | Tschirren et al. |
| 10,912,890 | B2 | 2/2021 | Gaillot et al. |
| 10,918,798 | B2 | 2/2021 | Helmer |

(56) References Cited

U.S. PATENT DOCUMENTS

| | | | |
|---|---|---|---|
| 10,967,128 B2 | 4/2021 | Holmqvist |
| 10,973,984 B2 | 4/2021 | Fournier et al. |
| 11,040,145 B1 | 6/2021 | Chu |
| 11,097,065 B2 | 8/2021 | Newton et al. |
| 11,103,647 B2 | 8/2021 | Bernhard et al. |
| 11,141,542 B2 | 10/2021 | Chu et al. |
| 11,147,932 B2 | 10/2021 | Alexandersson |
| 11,246,987 B2 | 2/2022 | Cowe et al. |
| 2003/0105430 A1 | 6/2003 | Lavi et al. |
| 2005/0222539 A1 | 10/2005 | Gonzales et al. |
| 2011/0196339 A1 | 8/2011 | Hirschel et al. |
| 2013/0331796 A1 | 12/2013 | Wozencroft |
| 2014/0128808 A1 | 5/2014 | Keitel |
| 2015/0088077 A1 | 3/2015 | Kemp et al. |
| 2015/0202379 A1 | 7/2015 | Raday et al. |
| 2015/0273162 A1 | 10/2015 | Holmqvist |
| 2016/0030675 A1 | 2/2016 | Draper et al. |
| 2016/0074584 A1 | 3/2016 | Carmel et al. |
| 2016/0074585 A1 | 3/2016 | Hommann et al. |
| 2016/0106929 A1 | 4/2016 | Fournier et al. |
| 2016/0129195 A1 | 5/2016 | Jennings et al. |
| 2016/0129200 A1 | 5/2016 | Jennings et al. |
| 2016/0151586 A1 | 6/2016 | Kemp |
| 2016/0175523 A1 | 6/2016 | Blomberg |
| 2016/0199588 A1 | 7/2016 | Kemp |
| 2016/0199589 A1 | 7/2016 | Plumptre |
| 2016/0220761 A1 | 8/2016 | Shetty et al. |
| 2016/0303323 A1 | 10/2016 | Saussaye et al. |
| 2016/0303327 A1 | 10/2016 | Moren |
| 2016/0317750 A1 | 11/2016 | Jugl et al. |
| 2016/0317753 A1 | 11/2016 | Jugl et al. |
| 2016/0325044 A1 | 11/2016 | Tschirren et al. |
| 2017/0007764 A1 | 1/2017 | Saussaye |
| 2017/0021103 A1 | 1/2017 | Mosebach et al. |
| 2017/0043103 A1 | 2/2017 | Wotton et al. |
| 2017/0072142 A1 | 3/2017 | Perthu |
| 2017/0080163 A1 | 3/2017 | Bendek et al. |
| 2017/0136192 A1 | 5/2017 | Stefansen et al. |
| 2017/0173270 A1 | 6/2017 | Nakamura et al. |
| 2017/0182242 A1 | 6/2017 | Galitz et al. |
| 2017/0203041 A1 | 7/2017 | Julian et al. |
| 2017/0224921 A1 | 8/2017 | Takabatake et al. |
| 2017/0252518 A1 | 9/2017 | Holmqvist |
| 2017/0258998 A1 | 9/2017 | Stamp |
| 2017/0290990 A1 | 10/2017 | Wu |
| 2017/0340824 A1 | 11/2017 | Maritan |
| 2017/0361015 A1 | 12/2017 | McCullough |
| 2017/0361021 A1 | 12/2017 | Wotton et al. |
| 2018/0015223 A1 | 1/2018 | Aeschlimann |
| 2018/0028753 A1 | 2/2018 | Wilmot et al. |
| 2018/0036491 A1 | 2/2018 | Maxfield |
| 2018/0036492 A1 | 2/2018 | Schader et al. |
| 2018/0043108 A1 | 2/2018 | Mesa et al. |
| 2018/0078713 A1 | 3/2018 | Hommann et al. |
| 2018/0079119 A1 | 3/2018 | Morris et al. |
| 2018/0093046 A1 | 4/2018 | Hourmand et al. |
| 2018/0099099 A1 | 4/2018 | Sund et al. |
| 2018/0110926 A1 | 4/2018 | Schrul et al. |
| 2018/0110936 A1 | 4/2018 | Hatch et al. |
| 2018/0126083 A1 | 5/2018 | Schmid et al. |
| 2018/0133407 A1 | 5/2018 | Kemp et al. |
| 2018/0140781 A1 | 5/2018 | Kemp et al. |
| 2018/0140782 A1 | 5/2018 | Kemp et al. |
| 2018/0147358 A1 | 5/2018 | Julian et al. |
| 2018/0154078 A1 | 6/2018 | Mosebach et al. |
| 2018/0154085 A1 | 6/2018 | Mosebach et al. |
| 2018/0154089 A1 | 6/2018 | Mosebach et al. |
| 2018/0161504 A1 | 6/2018 | Kemp et al. |
| 2018/0169342 A1 | 6/2018 | Mosebach et al. |
| 2018/0169349 A1 | 6/2018 | Mosebach et al. |
| 2018/0177952 A1 | 6/2018 | Bengtsson et al. |
| 2018/0200445 A1 | 7/2018 | Brereton et al. |
| 2018/0207363 A1 | 7/2018 | Fabien et al. |
| 2018/0221589 A1 | 8/2018 | Vogt et al. |
| 2018/0243506 A1 | 8/2018 | Niven et al. |
| 2018/0256826 A1 | 9/2018 | Roberts et al. |
| 2018/0264196 A1 | 9/2018 | Fabien et al. |
| 2018/0289899 A1 | 10/2018 | Gould |
| 2018/0296768 A1 | 10/2018 | Gould et al. |
| 2018/0304014 A1 | 10/2018 | Knudsen et al. |
| 2018/0311438 A1 | 11/2018 | Stamp et al. |
| 2018/0326152 A1 | 11/2018 | Laiosa |
| 2018/0344946 A1 | 12/2018 | Scharf |
| 2018/0353705 A1 | 12/2018 | Andre et al. |
| 2018/0369497 A1 | 12/2018 | Schader et al. |
| 2019/0151547 A1 | 5/2019 | Cowe et al. |
| 2019/0151564 A1 | 5/2019 | Schrul et al. |
| 2019/0151565 A1 | 5/2019 | Groetzbach et al. |
| 2019/0167908 A1 | 6/2019 | Fitzgibbon et al. |
| 2019/0201634 A1 | 7/2019 | Newton et al. |
| 2019/0209786 A1 | 7/2019 | Tschirren et al. |
| 2019/0240394 A1 | 8/2019 | Horvath et al. |
| 2019/0269856 A1 | 9/2019 | Baumeyer et al. |
| 2020/0009323 A1 | 1/2020 | Nair et al. |
| 2020/0030539 A1 | 1/2020 | Shabudin, Jr. |
| 2020/0030547 A1 | 1/2020 | Wang et al. |
| 2020/0033069 A1 | 1/2020 | Nakamura et al. |
| 2020/0035047 A1 | 1/2020 | Arnold |
| 2020/0046910 A1 | 2/2020 | Maxfield et al. |
| 2020/0061309 A1 | 2/2020 | Alexandersson |
| 2020/0139046 A1 | 5/2020 | Jacobsen |
| 2020/0147311 A1 | 5/2020 | Dugand et al. |
| 2020/0164138 A1 | 5/2020 | Holmqvist |
| 2020/0254181 A1 | 8/2020 | Mosebach et al. |
| 2020/0289740 A1 | 9/2020 | Tamtoro et al. |
| 2020/0330699 A1 | 10/2020 | Burren et al. |
| 2021/0015741 A1 | 1/2021 | Wotton et al. |
| 2021/0085884 A1 | 3/2021 | Liniger et al. |
| 2021/0093790 A1 | 4/2021 | Mosebach et al. |
| 2021/0106756 A1 | 4/2021 | Alexandersson |
| 2021/0268201 A1 | 9/2021 | Boström |
| 2021/0275750 A1 | 9/2021 | Helmer et al. |
| 2022/0016359 A1 | 1/2022 | Alexandersson |

FOREIGN PATENT DOCUMENTS

| | | |
|---|---|---|
| CN | 105188807 B | 12/2017 |
| DE | 102004060146 C5 | 12/2015 |
| EP | 2083887 B1 | 2/2011 |
| EP | 2323717 B1 | 5/2013 |
| EP | 2525845 B1 | 8/2014 |
| EP | 2588168 B1 | 3/2015 |
| EP | 2731653 B1 | 10/2015 |
| EP | 2931338 B1 | 11/2016 |
| EP | 3235530 A1 | 10/2017 |
| EP | 3320932 A1 | 5/2018 |
| EP | 3107605 B1 | 9/2018 |
| EP | 2654854 B1 | 10/2018 |
| EP | 1850892 B1 | 1/2019 |
| EP | 3541453 | 9/2019 |
| EP | 2953667 B1 | 10/2019 |
| EP | 3407939 B1 | 10/2019 |
| EP | 3490647 B1 | 10/2021 |
| JP | 2013534164 A | 9/2013 |
| JP | 2015516845 A | 6/2015 |
| JP | 2017525420 A | 9/2017 |
| KR | 1020150097784 A | 8/2015 |
| KR | 1020170048508 A | 5/2017 |
| RU | 2671419 C2 | 10/2018 |
| WO | 03041768 A1 | 5/2003 |
| WO | 2003047663 A3 | 6/2003 |
| WO | 2004098687 A1 | 11/2004 |
| WO | 2005097238 A3 | 10/2005 |
| WO | 2008059233 A1 | 5/2008 |
| WO | 2009019436 A1 | 2/2009 |
| WO | 2009019437 A1 | 2/2009 |
| WO | 2009019438 A1 | 2/2009 |
| WO | 2009019439 A1 | 2/2009 |
| WO | 2009019440 A1 | 2/2009 |
| WO | 2009081103 A1 | 7/2009 |
| WO | 2009090499 A2 | 7/2009 |
| WO | 2009143255 A1 | 11/2009 |
| WO | 2012045350 A1 | 4/2012 |
| WO | 2012164397 A1 | 12/2012 |

(56)     References Cited

FOREIGN PATENT DOCUMENTS

| WO | 2013006119 A1 | 1/2013 |
|----|---------------|--------|
| WO | 2013152323 A1 | 10/2013 |
| WO | 2015132234 A1 | 9/2015 |
| WO | 2016193344 A1 | 12/2016 |
| WO | 2016193346 A1 | 12/2016 |
| WO | 2017089269 A1 | 6/2017 |
| WO | 2017187177 A1 | 11/2017 |
| WO | 2017223354 A1 | 12/2017 |
| WO | 2018004842 A1 | 1/2018 |
| WO | 2018010947 A1 | 1/2018 |
| WO | 2018018164 A1 | 2/2018 |
| WO | 2018018165 A1 | 2/2018 |
| WO | 2018018167 A1 | 2/2018 |
| WO | 2018037034 A1 | 3/2018 |
| WO | 2018053657 A1 | 3/2018 |
| WO | 2018060745 A1 | 4/2018 |
| WO | 2018069031 A1 | 4/2018 |
| WO | 2018082886 A1 | 5/2018 |
| WO | 2018091262 A1 | 5/2018 |
| WO | 2018167640 A1 | 9/2018 |
| WO | 2018172223 A1 | 9/2018 |
| WO | 2018178127 A8 | 10/2018 |
| WO | 2018192750 A1 | 10/2018 |
| WO | 2018197774 A1 | 11/2018 |
| WO | 2018206583 A1 | 11/2018 |
| WO | 2018215271 A1 | 11/2018 |
| WO | 2018226565 A1 | 12/2018 |
| WO | 2020015986 A1 | 1/2020 |

320

1

AUTO-INJECTOR WITH NEEDLE COVER

CROSS-REFERENCE TO RELATED APPLICATIONS

This application is the United States national phase of International Application No. PCT/EP2020/055003 filed Feb. 26, 2020, and claims priority to Europe patent Application No. 19305226.3 filed Feb. 26, 2019, the entire disclosures of which are hereby incorporated by reference in their entirety.

BACKGROUND OF THE INVENTION

Field of the Disclosure

The present disclosure relates generally to a drug delivery device and, more specifically, to an auto-injector.

Description of the Related Art

Various types of automatic injection devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism that can be triggered by the user. Many of these devices, such as auto-injectors, are designed so that the reservoir, such as a pre-filled syringe, is assembled into the device during assembly of the device. In addition to automatically deploying the needle-injection mechanism, many drug delivery devices also automatically shield the needle after use of the device to prevent any unintended contact with the needle.

SUMMARY OF THE INVENTION

In one aspect, a drug delivery device includes a housing, a syringe assembly comprising a barrel, a stopper, and a cannula, with at least a portion of the syringe assembly positioned within the housing, a drive assembly configured to move the stopper within the barrel upon actuation of the drive assembly, with at least a portion of the drive assembly positioned within the housing, a lever actuation member moveable between a locked position where actuation of the drive assembly is prevented and a released position where actuation of the drive assembly is allowed, and a needle cover having a pre-use position where the cannula is positioned within the needle cover, an actuation position where the drive assembly is actuated, and a post-use position where the cannula is positioned within the needle cover. The needle cover configured to engage the lever actuation member and move the lever actuation member to the released position when the needle cover is in the actuation position.

The device may further include a syringe holder moveable relative to the housing between a first position and a second position, the syringe assembly received by the syringe holder. The syringe holder is configured to move from the first position to the second position when the needle cover is in the actuation position, with a portion of the cannula of the syringe assembly extending outside of the needle cover when the syringe holder is in the second position and when the needle cover is in the actuation position. A portion of the needle cover may engage a cover stop of the syringe holder to restrict axial movement of the needle cover in at least one direction when the needle cover is in the pre-use position. The drive assembly may include a plunger body having a plunger rod portion and a drive member, with the drive member configured to move the plunger body within the housing. A longitudinal axis of the plunger rod may be spaced from and parallel to a longitudinal axis of the drive member. The drive member may be a compression spring. The drive assembly may further include a plunger rod cover positioned over at least a portion of the plunger rod portion, with the plunger rod cover configured to engage the stopper of the syringe assembly. The drive assembly may further include a spring guide member, with the drive member positioned over the spring guide member.

The needle cover may prevent movement of the lever actuation member from the locked position to the released position when the needle cover is in the pre-use position.

The lever actuation member may be rotatable about a rotation axis between the locked position and the released position. The lever actuation member may include a restriction surface configured to engage the needle cover and restrict rotation of the lever actuation member when the needle cover is in the pre-use position. The restriction surface of the lever actuation member may be spaced from the needle cover to form a gap when the needle cover is in the pre-use position. The needle cover may include a lever contact portion and the lever actuation member may include a needle cover contact surface, with the lever contact portion of the needle cover configured to engage the needle cover contact surface of the lever actuation member and rotate the lever actuation member about the rotation axis from the locked position to the released position when the needle cover is in the actuation position. The lever actuation member may define a recessed area configured to receive a portion of the lever contact portion of the needle cover when the needle cover is in the actuation position. The lever contact portion of the needle cover may define a cylindrical surface and the needle cover contact surface of the lever actuation member may define a planar surface.

The device may further include a motor body receiving at least a portion of the drive assembly, where the motor body includes a stop surface and the lever actuation member includes a motor body contact surface. The motor body contact surface of the lever actuation member may be engaged with the stop surface of the motor body when the lever actuation member is in the locked position and disengaged from the stop surface of the motor body when the lever actuation member is in the released position. The stop surface of the motor body may define a planar surface and the motor body contact surface of the lever actuation member may define a cylindrical surface.

The device may include one or several of the following features, taken individually or according to all technical possible combinations:

a drug delivery device may comprise: a housing; a syringe assembly comprising a barrel, a stopper, and a cannula, at least a portion of the syringe assembly positioned within the housing; a drive assembly configured to move the stopper within the barrel upon actuation of the drive assembly, at least a portion of the drive assembly positioned within the housing; a lever actuation member moveable between a locked position where actuation of the drive assembly is prevented and a released position where actuation of the drive assembly is allowed; and a needle cover having a pre-use position where the cannula is positioned within the needle cover, an actuation position where the drive assembly is actuated, and a post-use position where the cannula is positioned within the needle cover, the needle cover configured to engage the lever actuation member and move the lever actuation member to the released position when the needle cover is in the actuation position;

the drug delivery device may further include a syringe holder moveable relative to the housing between a first position and a second position, the syringe assembly received by the syringe holder;

the syringe holder may be configured to move from the first position to the second position when the needle cover is in the actuation position, a portion of the cannula of the syringe assembly extending outside of the needle cover when the syringe holder is in the second position and when the needle cover is in the actuation position;

a portion of the needle cover may engage a cover stop of the syringe holder to restrict axial movement of the needle cover in at least one direction when the needle cover is in the pre-use position;

the drive assembly may comprise a plunger body having a plunger rod portion and a drive member, the drive member is configured to move the plunger body within the housing;

a longitudinal axis of the plunger rod portion may be spaced from and parallel to a longitudinal axis of the drive member;

the drive member may comprise a compression spring;

the drive assembly may comprise a plunger rod cover positioned over at least a portion of the plunger rod portion, the plunger rod cover configured to engage the stopper of the syringe assembly;

the drive assembly may comprise a spring guide member, the drive member positioned over the spring guide member;

the needle cover may prevent movement of the lever actuation member from the locked position to the released position when the needle cover is in the pre-use position;

the lever actuation member may be rotatable about a rotation axis between the locked position and the released position;

the lever actuation member may include a restriction surface configured to engage the needle cover and restrict rotation of the lever actuation member when the needle cover is in the pre-use position;

the restriction surface of the lever actuation member may be spaced from the needle cover to form a gap when the needle cover is in the pre-use position;

the needle cover may comprise a lever contact portion and the lever actuation member comprises a needle cover contact surface, the lever contact portion of the needle cover is configured to engage the needle cover contact surface of the lever actuation member and rotate the lever actuation member about the rotation axis from the locked position to the released position when the needle cover is in the actuation position;

the lever actuation member may define a recessed area configured to receive a portion of the lever contact portion of the needle cover when the needle cover is in the actuation position;

the lever contact portion of the needle cover may define a cylindrical surface and the needle cover contact surface of the lever actuation member defines a planar surface;

the motor body may receive at least a portion of the drive assembly, wherein the motor body comprises a stop surface and the lever actuation member comprises a motor body contact surface, the motor body contact surface of the lever actuation member engaged with the stop surface of the motor body when the lever actuation member is in the locked position and disengaged from the stop surface of the motor body when the lever actuation member is in the released position;

the stop surface of the motor body may define a planar surface and the motor body contact surface of the lever actuation member defines a cylindrical surface.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

5

Figure 17:
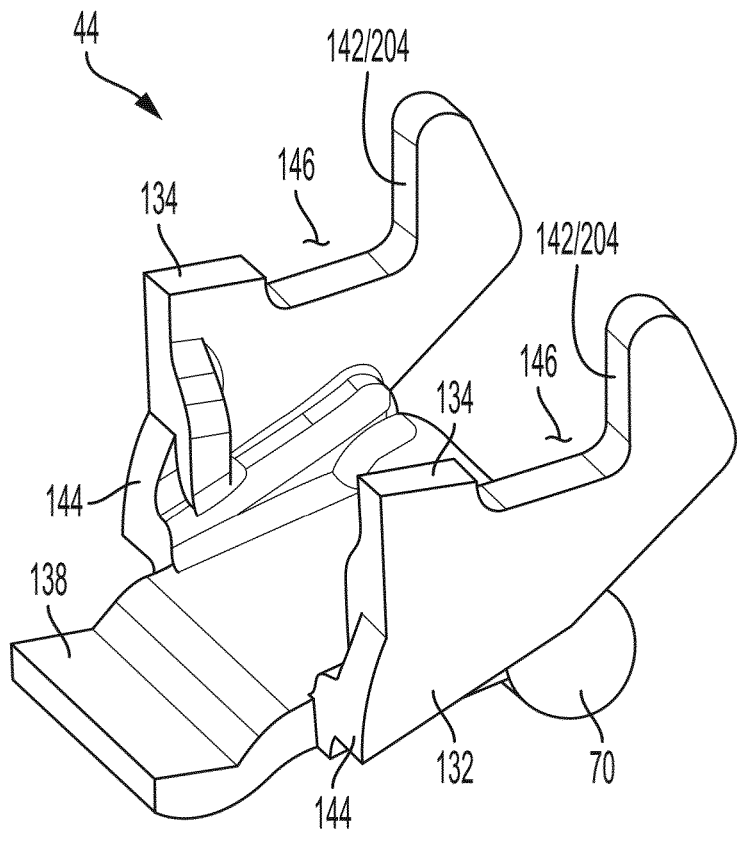
FIG. 17 is a perspective view of a lever actuation member of the drug delivery device of FIG. 1.
Figure 18:
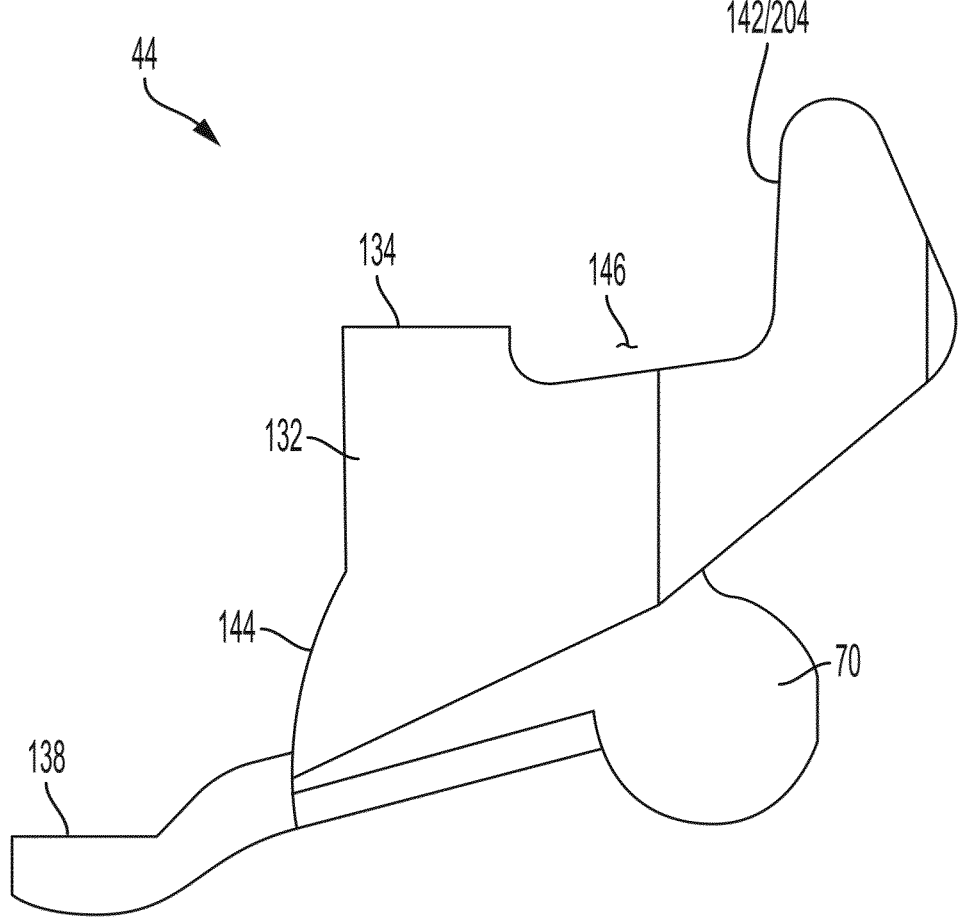

FIG. 18 is a cross-sectional view of the lever actuation member of FIG. 17.

Figure 1A:
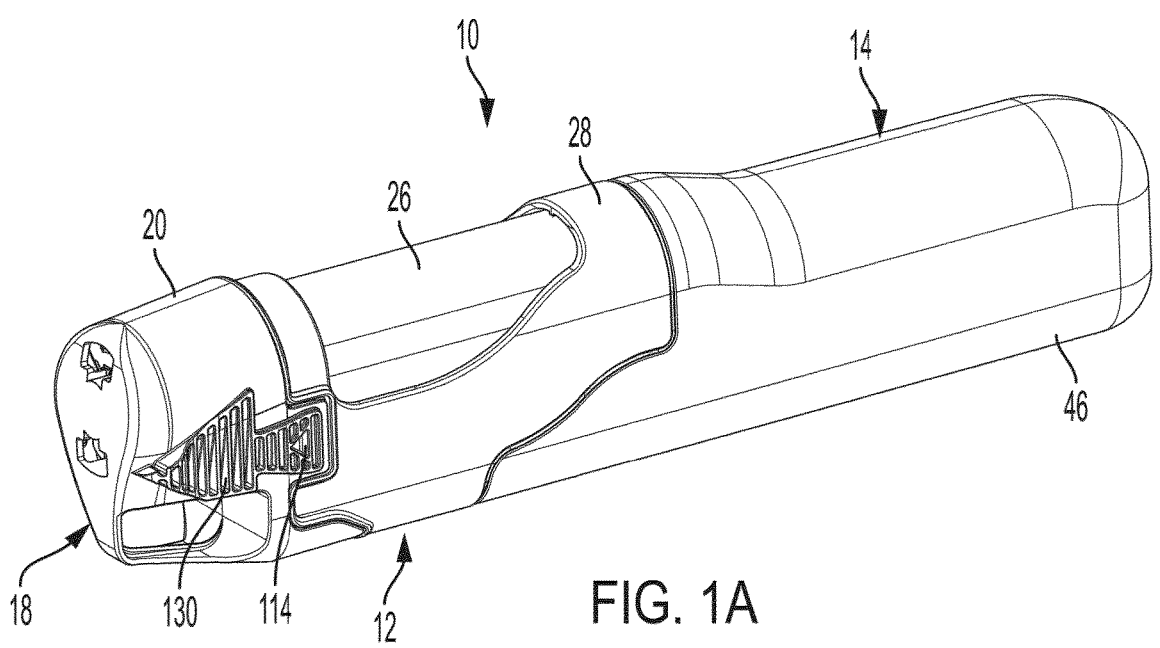
FIG. 1A is a perspective view of a drug delivery device according to one aspect of the present application, showing a storage position of the device.
Figure 1B:
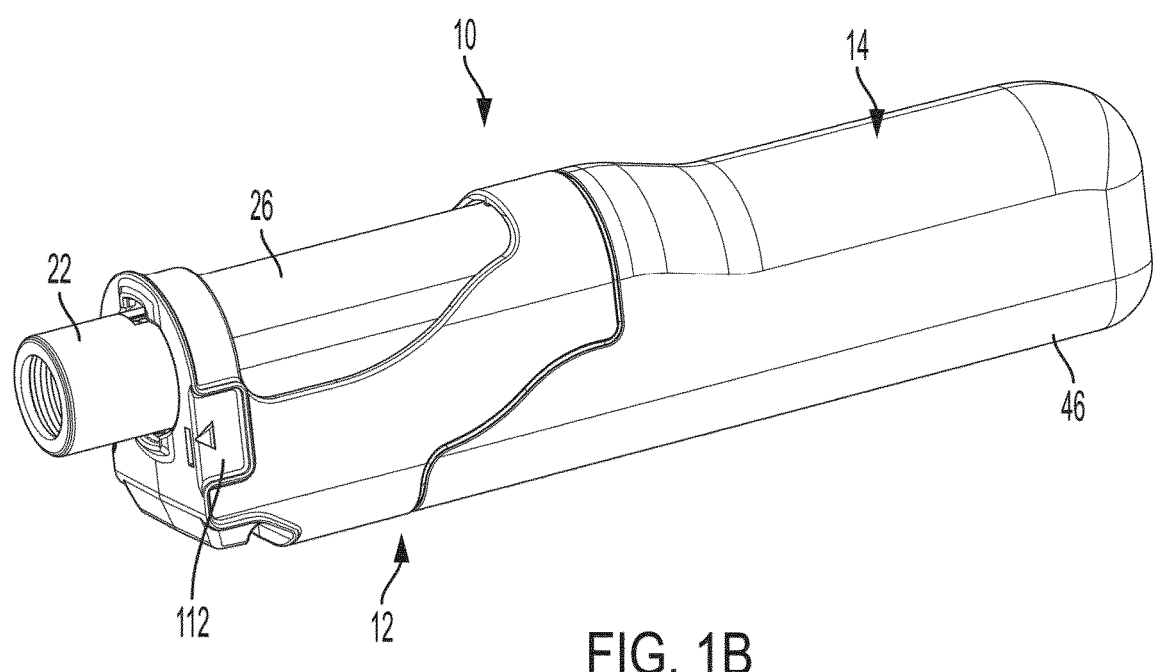
FIG. 1B is a perspective view of the drug delivery device of FIG. 1, showing a pre-use position of the device.
Figure 19A:
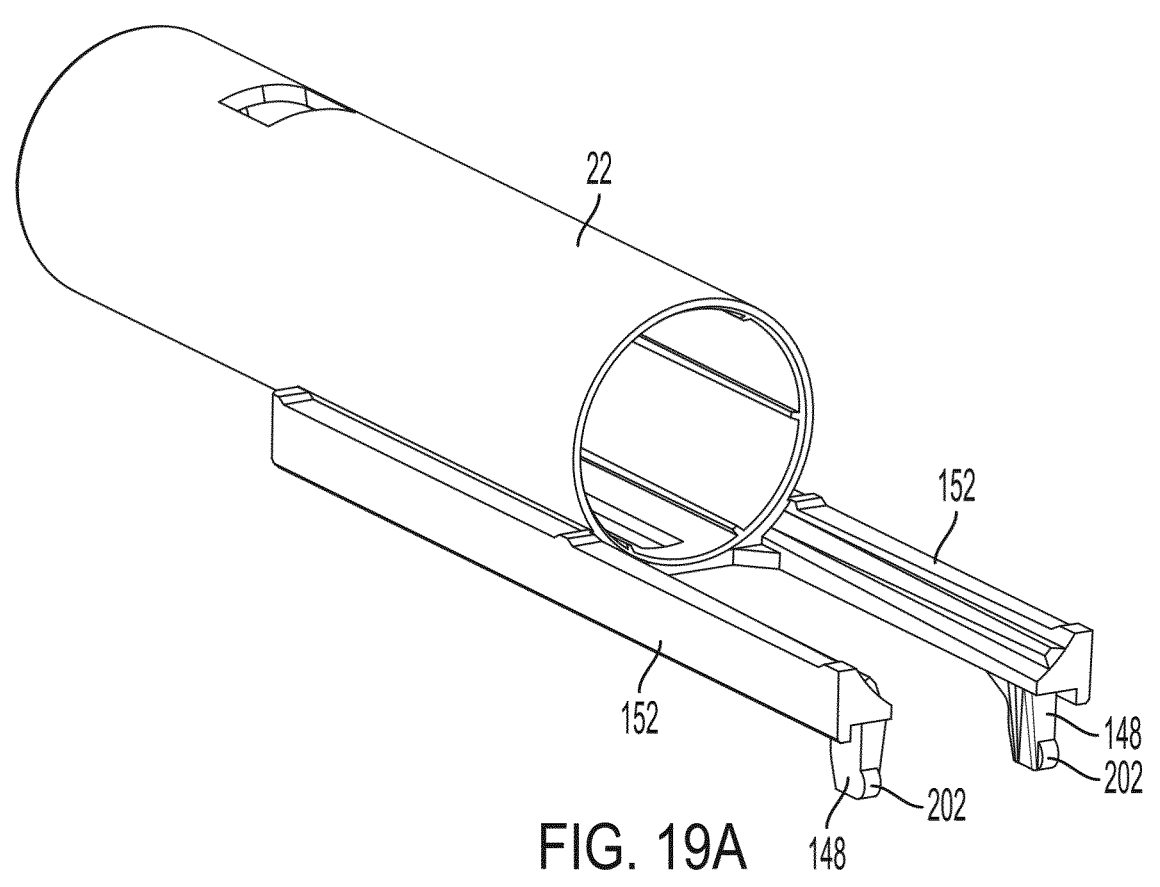

FIG. 19A is a perspective view of a needle cover of the drug delivery device of FIG. 1.

Figure 19B:
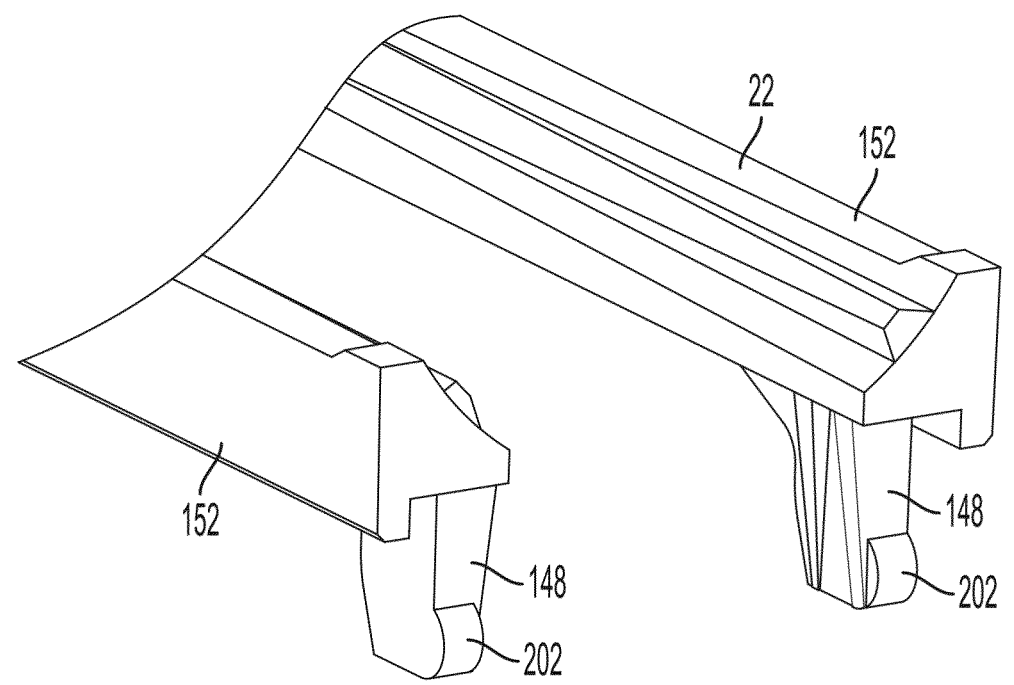

FIG. 19B is a partial perspective view of the needle cover of FIG. 19A.

Figure 20:
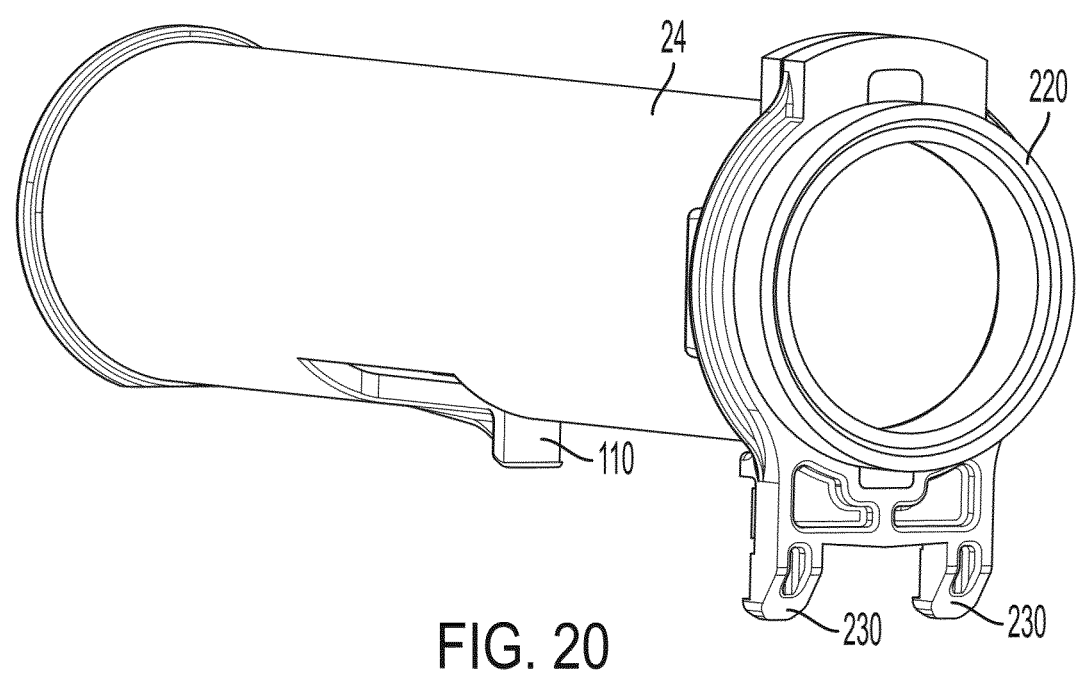

FIG. 20 is a perspective view of a syringe holder of the drug delivery device of FIG. 1.

Figure 21:
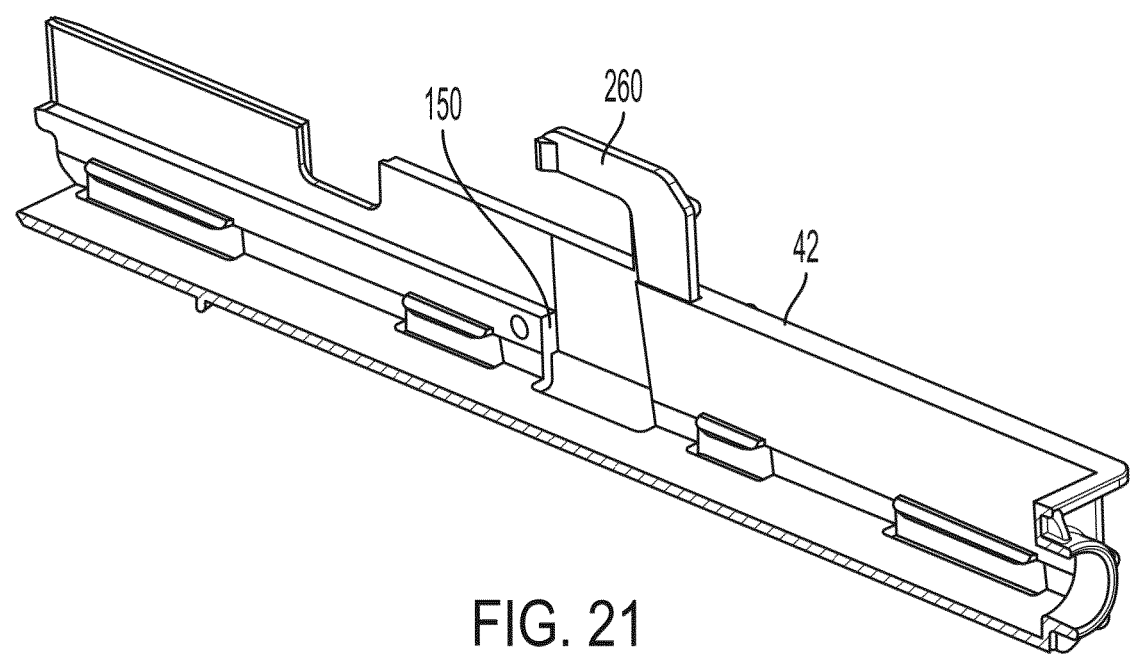

FIG. 21 is a perspective cross-sectional view of a motor body of the drug delivery device of FIG. 1.

Figure 22:
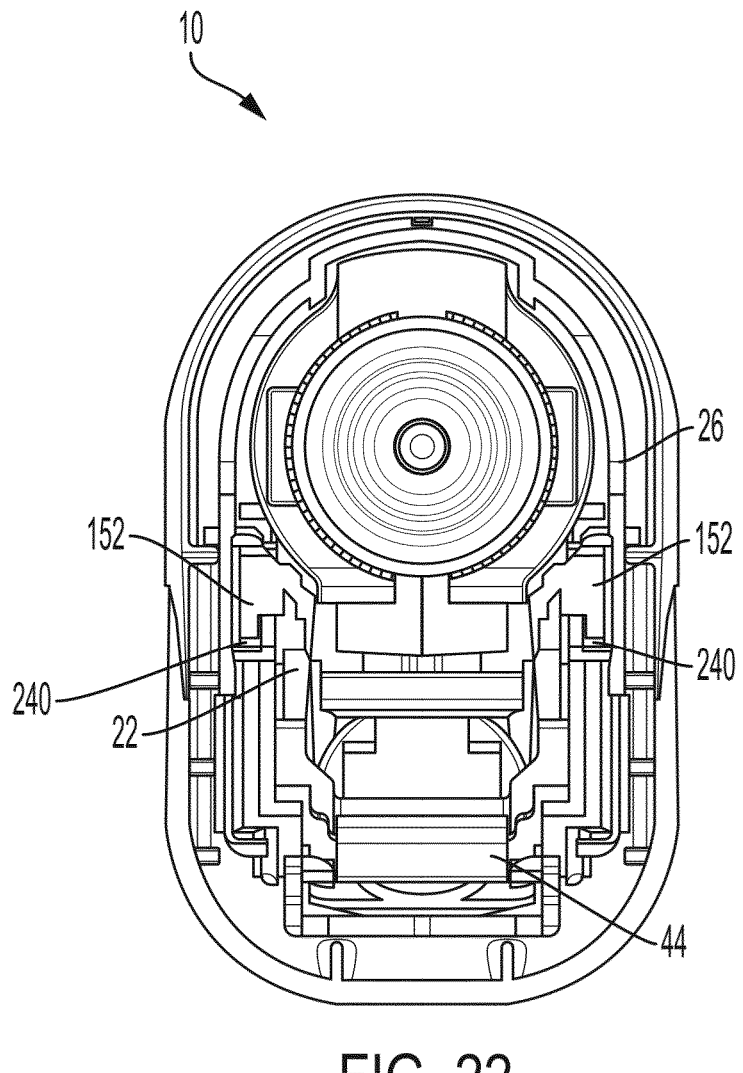

FIG. 22 is a cross-sectional view of the drug delivery device of FIG. 1, showing a guiding groove of a cassette body.

Figure 23:
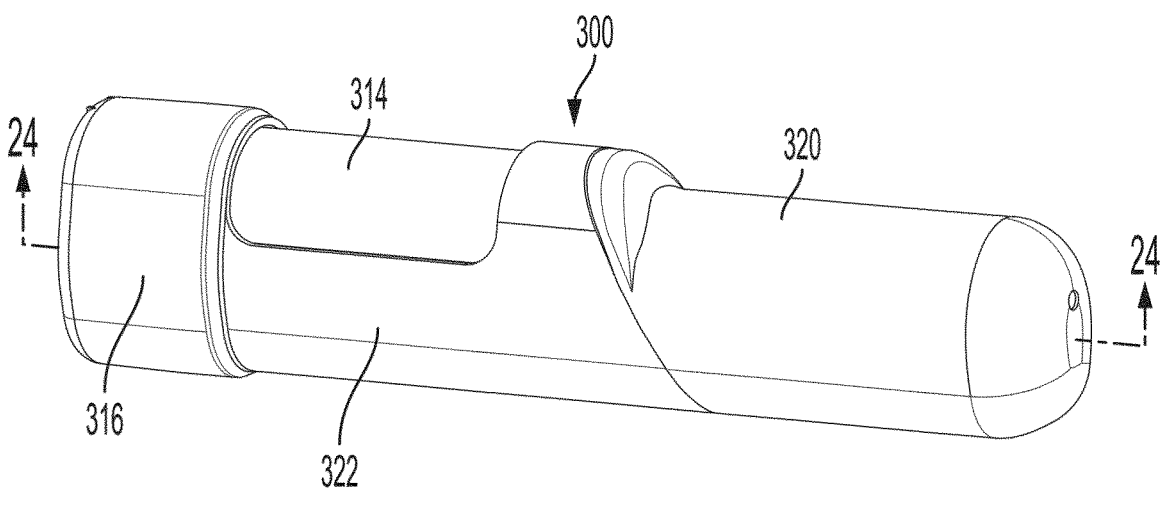

FIG. 23 is a perspective view of a drug delivery device according to a further aspect of the present application, showing a storage position of the device.

Figure 24:
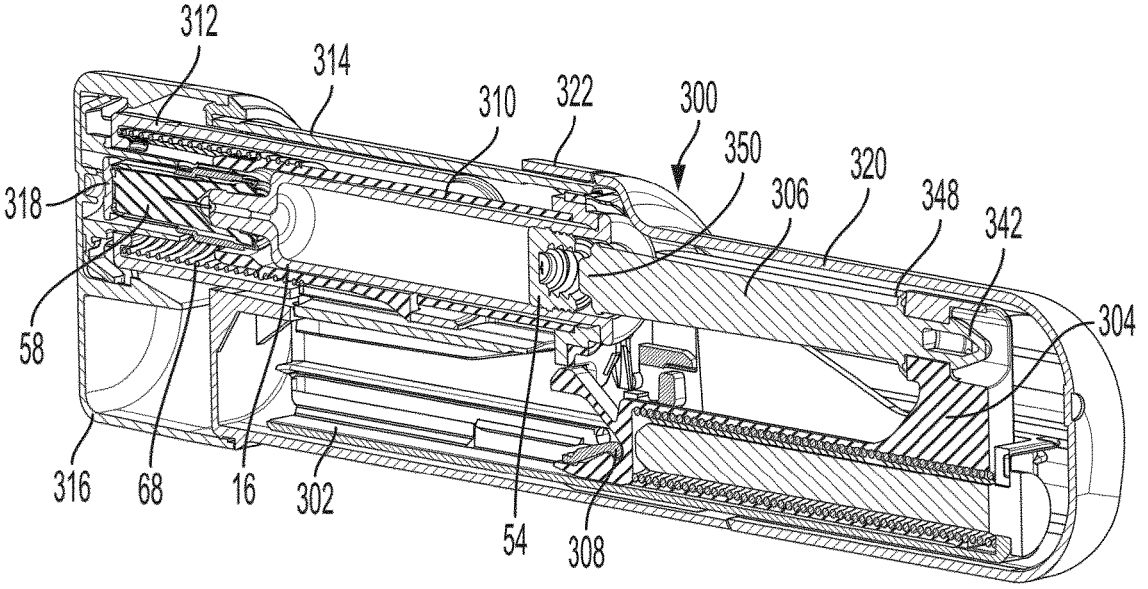

FIG. 24 is a cross-sectional view taken along line 24-24 shown in FIG. 23.

Figure 25:
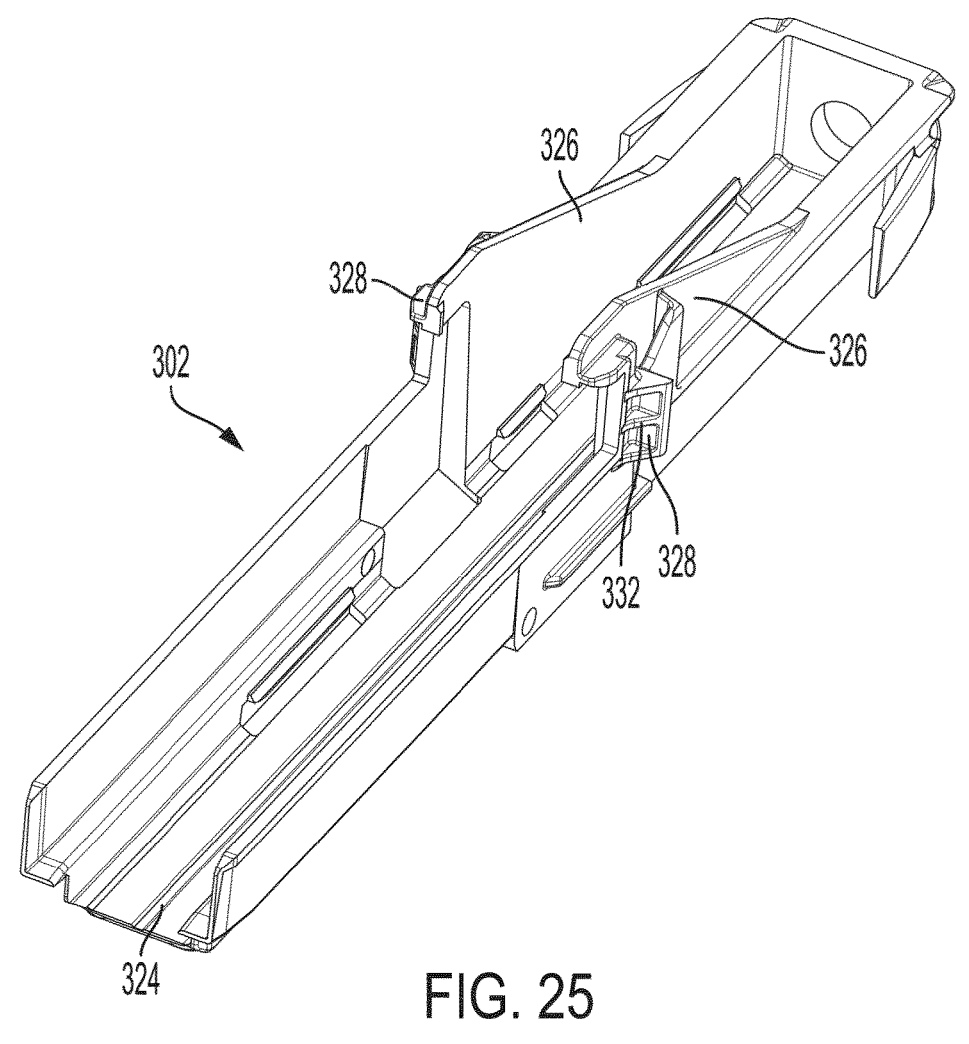

FIG. 25 is a top perspective view of a motor body of the drug delivery device of FIG. 23.

Figure 26:
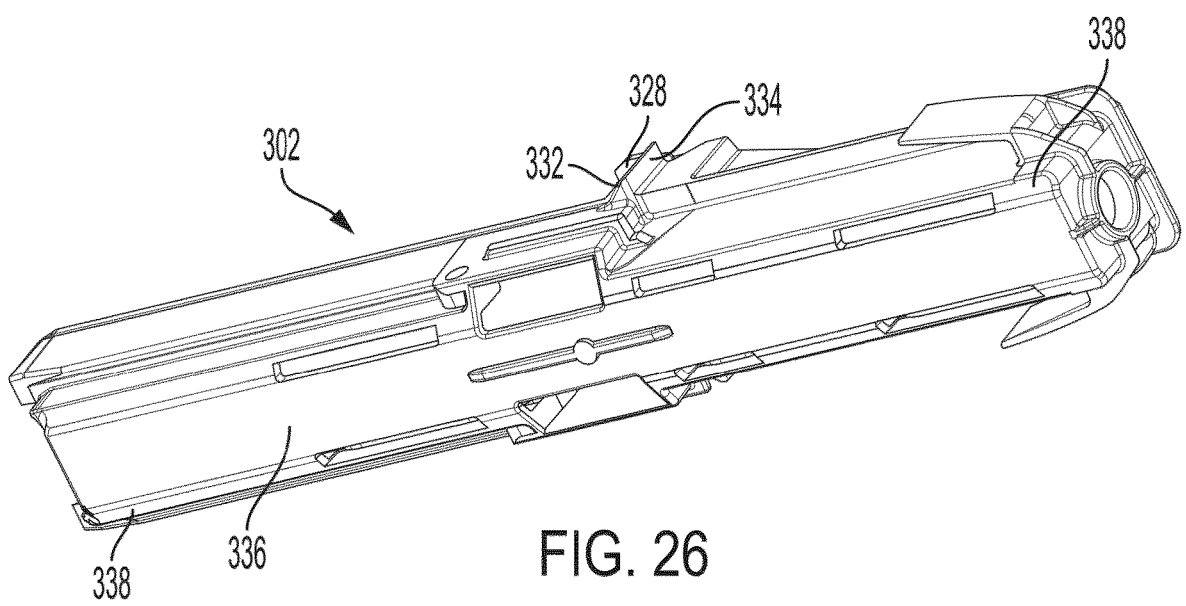

FIG. 26 is a bottom perspective view of the motor body of FIG. 25.

Figures 27, 28:
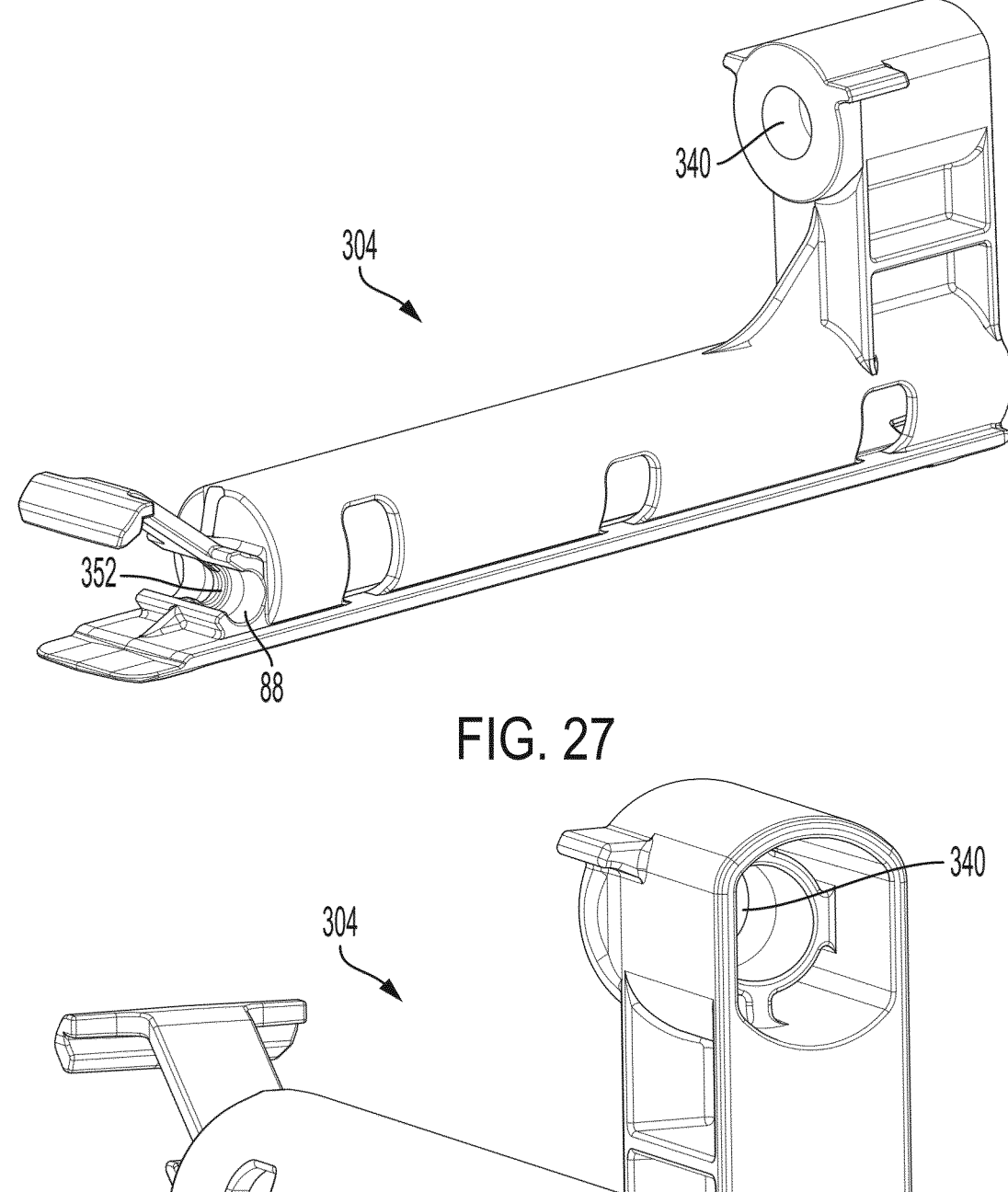

FIG. 27 is a front perspective view of a plunger body of the drug delivery device of FIG. 23.

FIG. 28 is a rear perspective view of the plunger body of FIG. 27.

Figure 29:
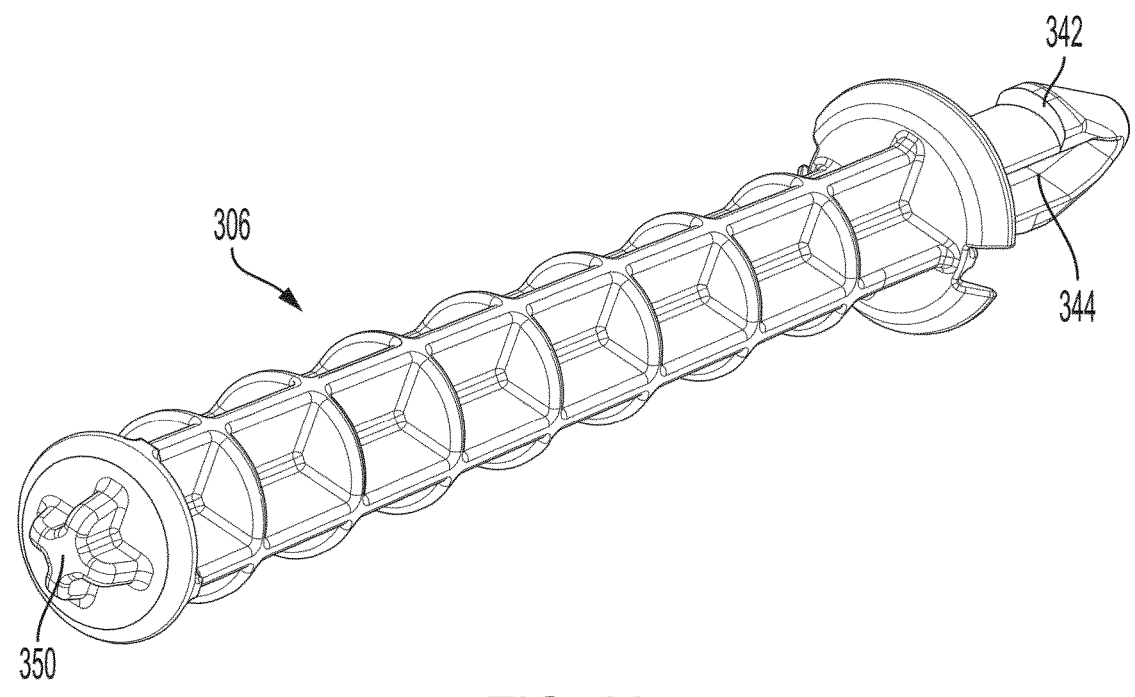

FIG. 29 is a front perspective view of a plunger rod portion of the drug delivery device of FIG. 23.

Figure 30:
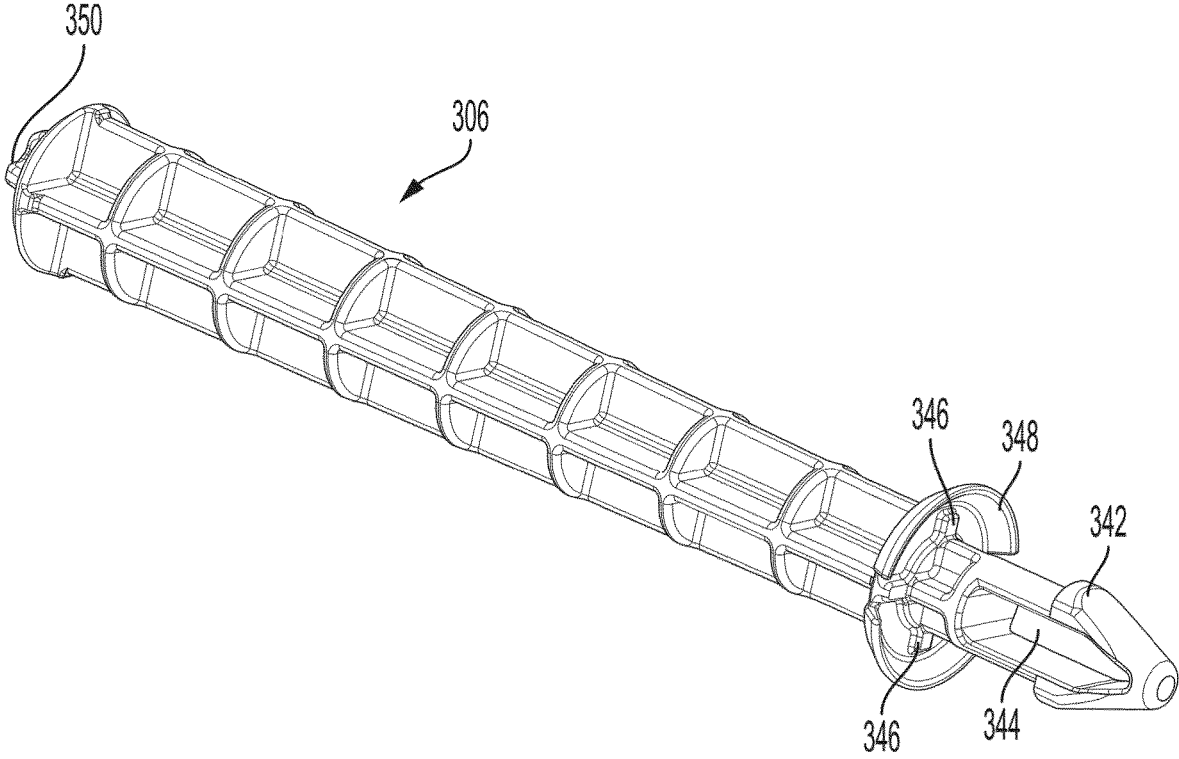

FIG. 30 is a rear perspective view of the plunger rod portion of FIG. 29.

Figure 31:
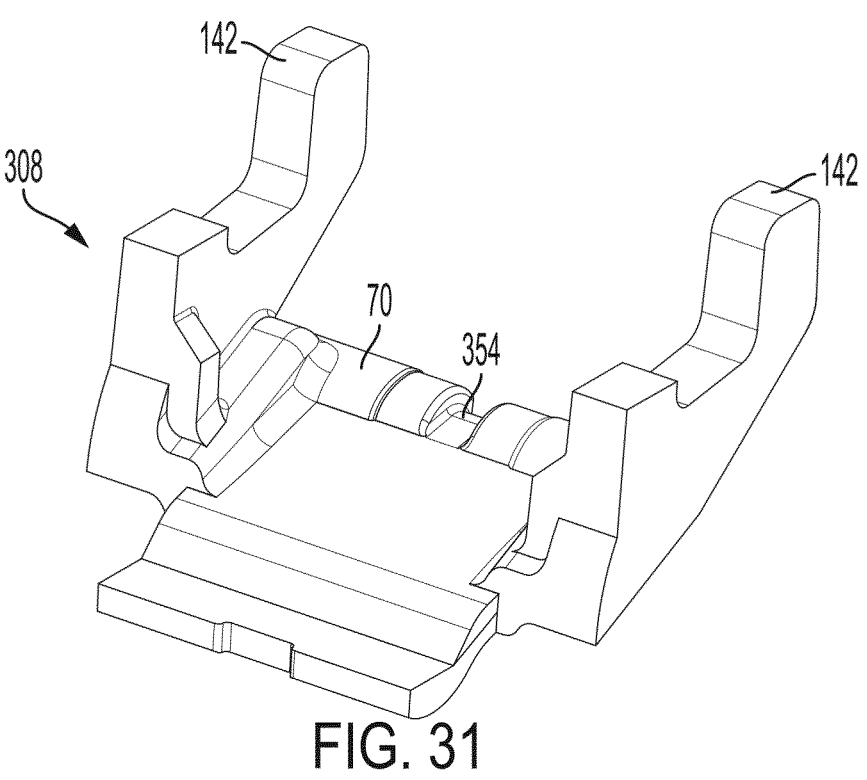

FIG. 31 is a top perspective view of a lever actuation member of the drug delivery device of FIG. 23.

Figure 32:
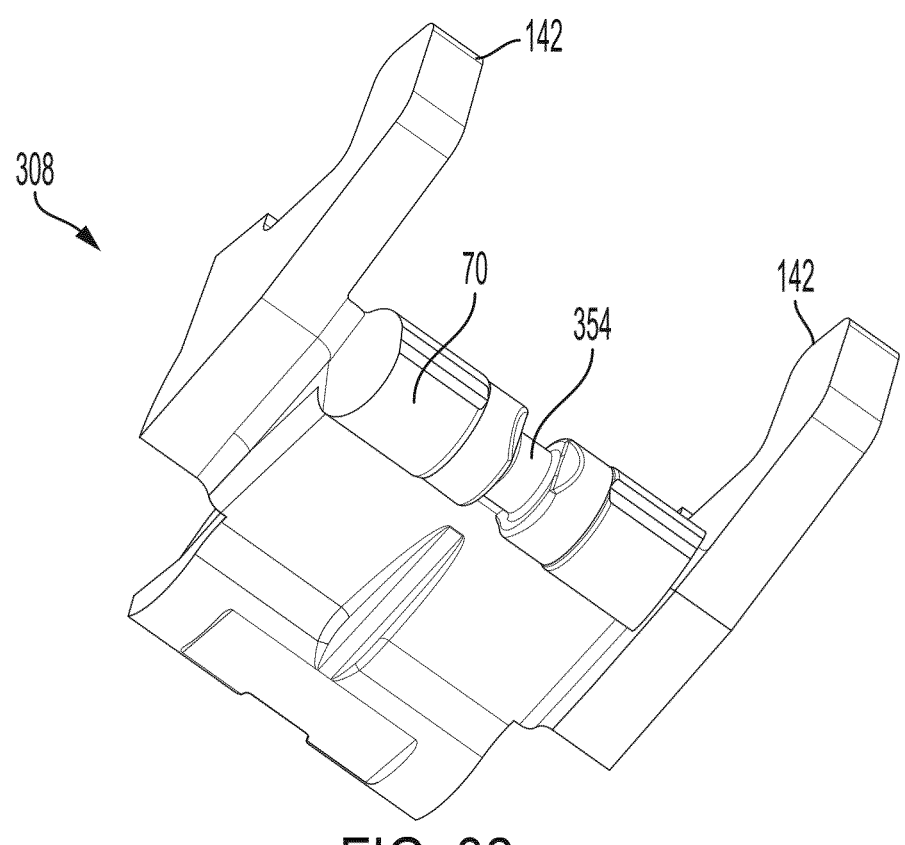

FIG. 32 is a bottom perspective view of the lever actuation member of the drug delivery device of FIG. 31.

Figures 33, 34:
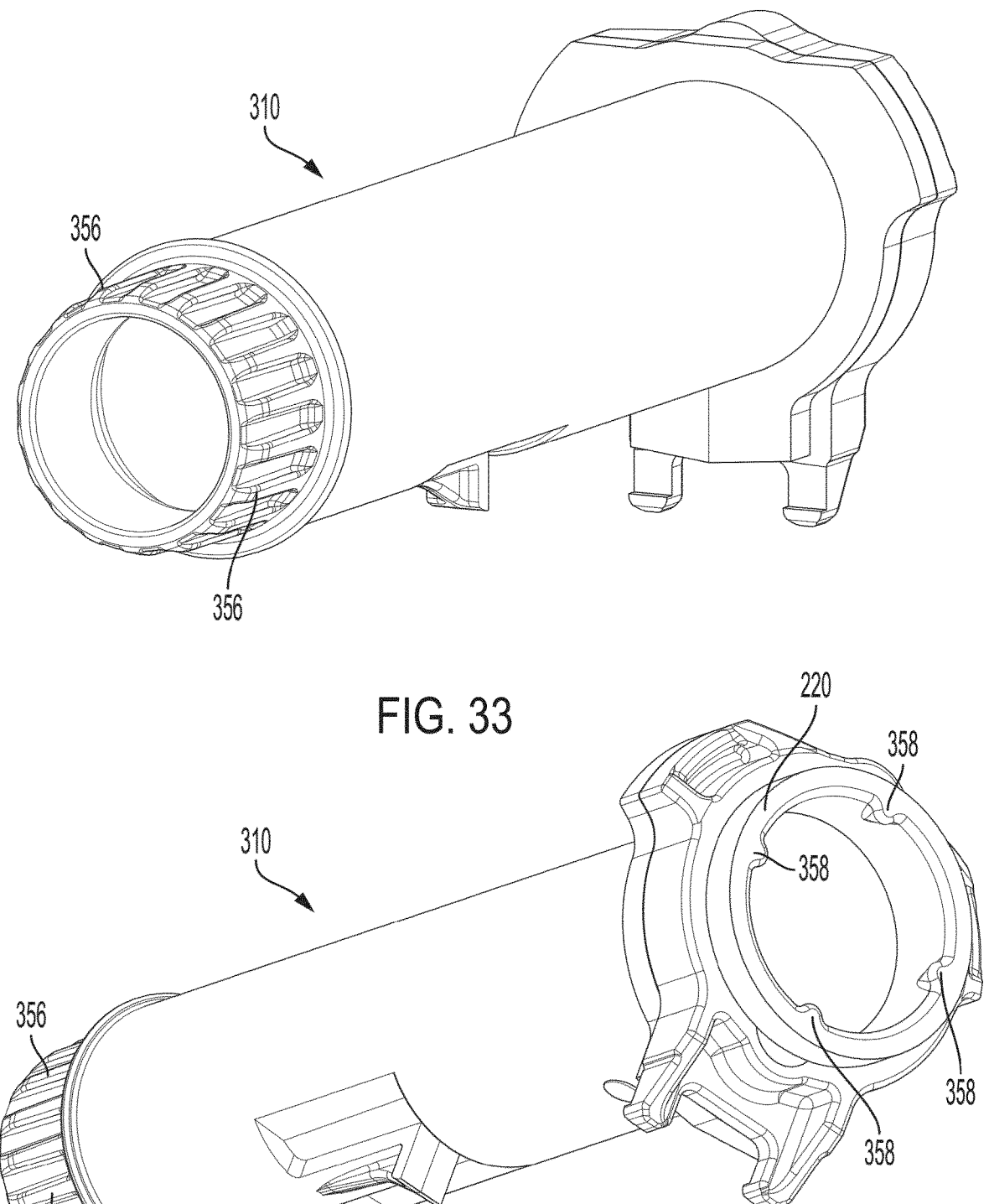

FIG. 33 is a front perspective view of a syringe holder of the drug delivery device of FIG. 23.

FIG. 34 is a rear perspective view of the syringe holder of the drug delivery device of FIG. 33.

Figure 35:
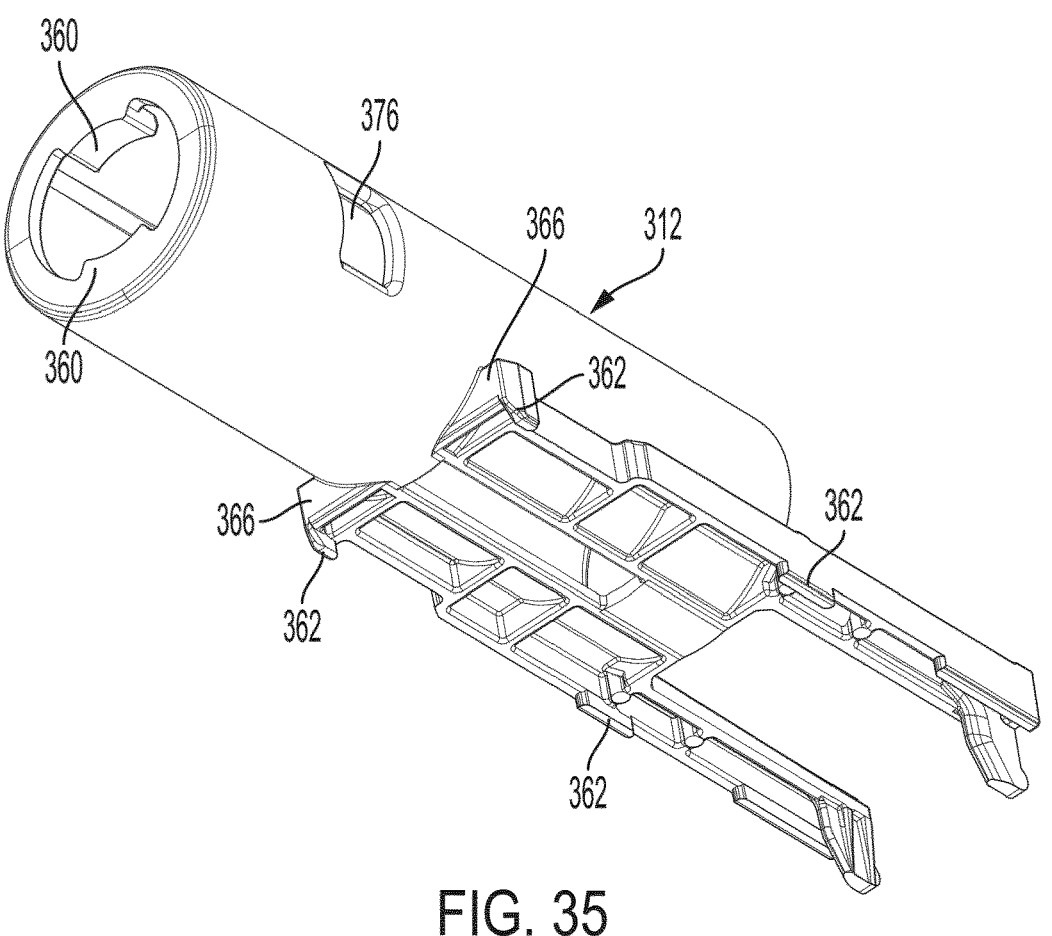

FIG. 35 is a front perspective view of a needle cover of the drug delivery device of FIG. 23.

Figure 36:
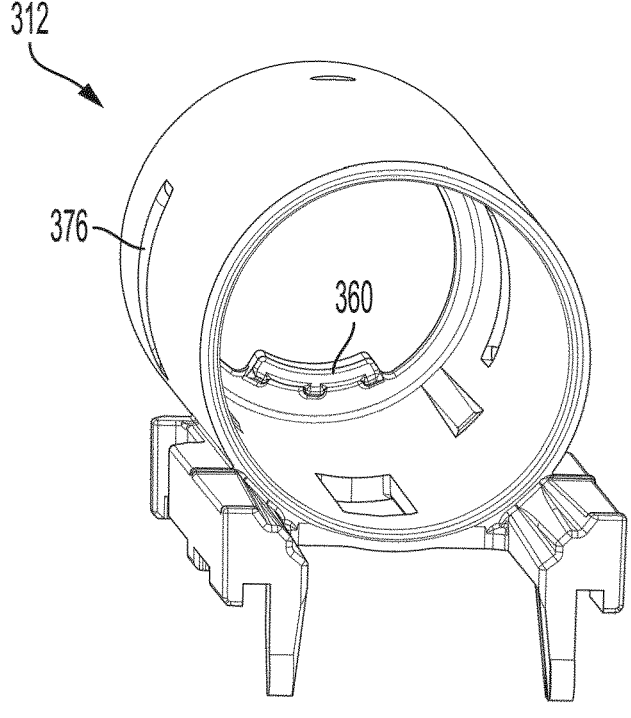

FIG. 36 is a rear perspective view of the needle cover of the drug delivery device of FIG. 35.

Figures 37, 38:
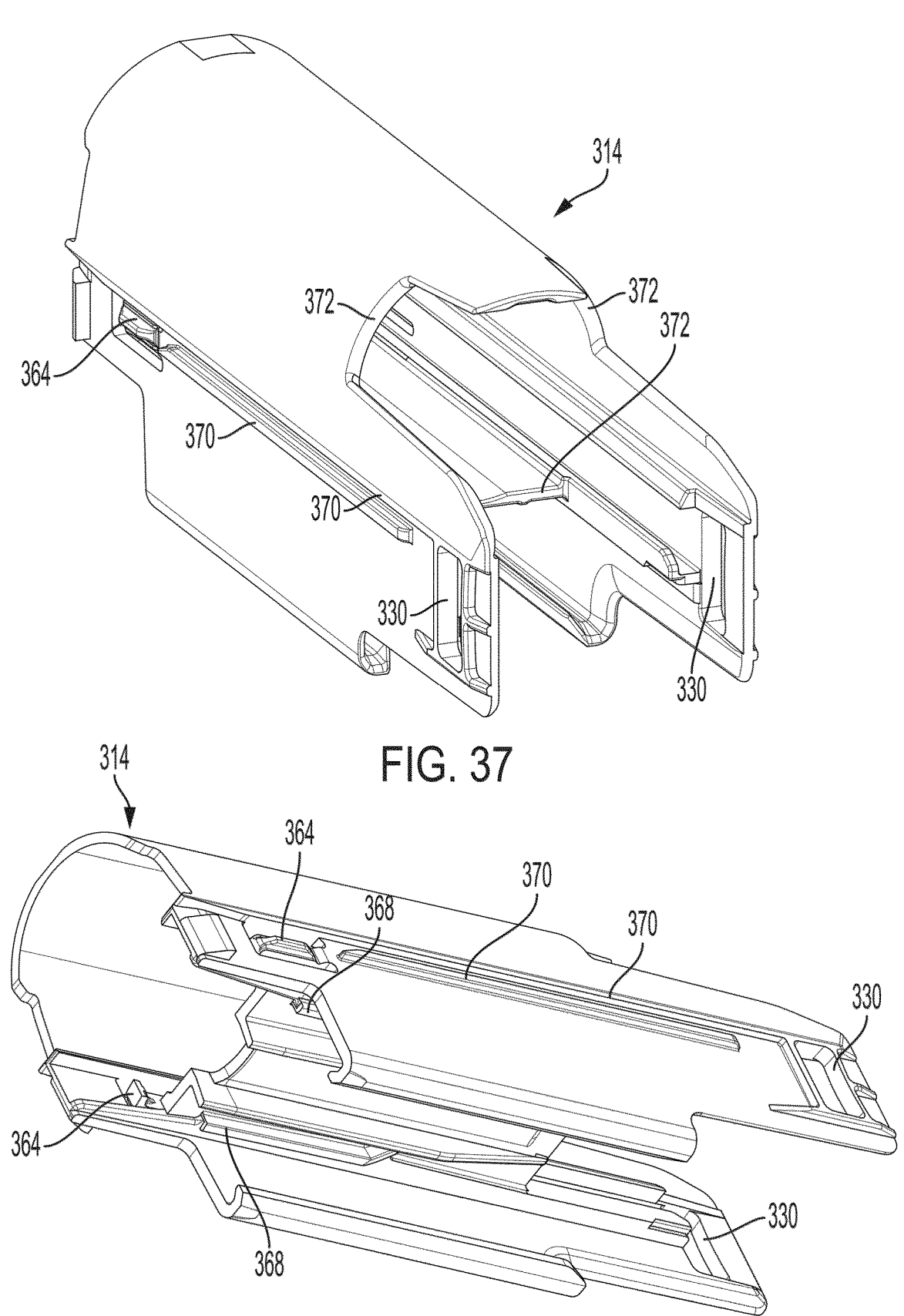

FIG. 37 is a top perspective view of a cassette body of the drug delivery device of FIG. 23.

FIG. 38 is a bottom perspective of the cassette body of the drug delivery device of FIG. 37.

Figure 39:
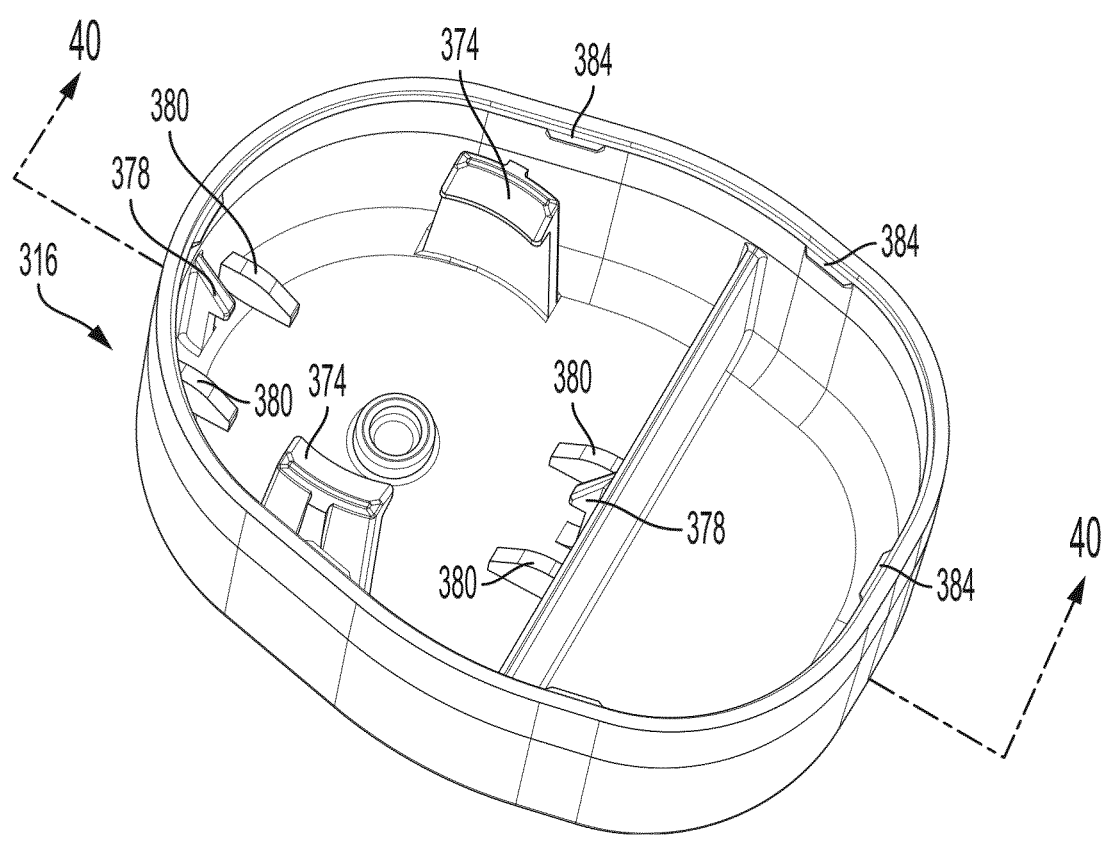

FIG. 39 is a top perspective view of a cap of the drug delivery device of FIG. 23.

Figure 40:
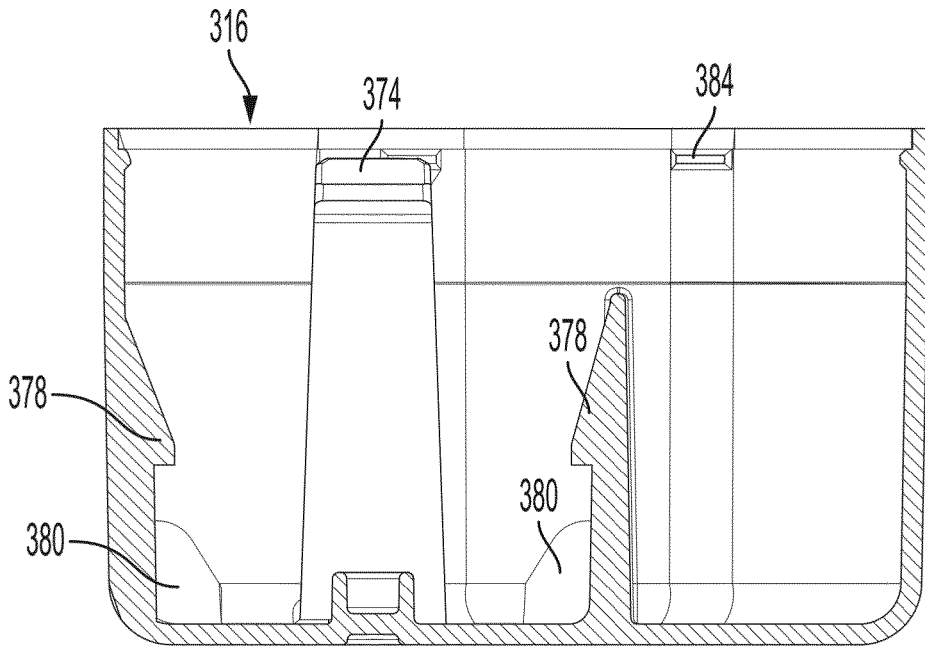

FIG. 40 is a cross-sectional view taken along line 40-40 in FIG. 39.

Figure 41:
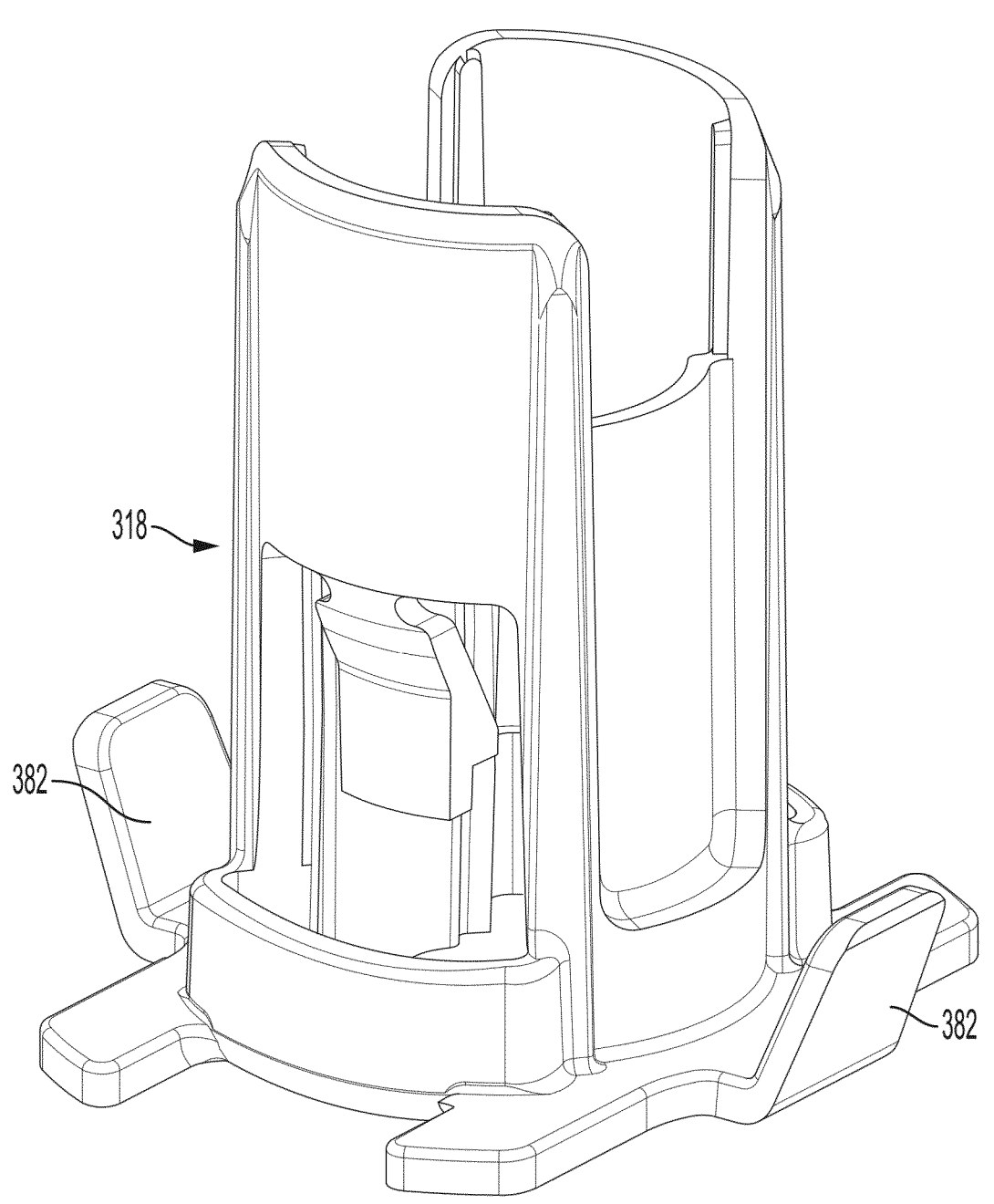

FIG. 41 is a perspective view of a retainer of the drug delivery device of FIG. 23.

Figure 42:
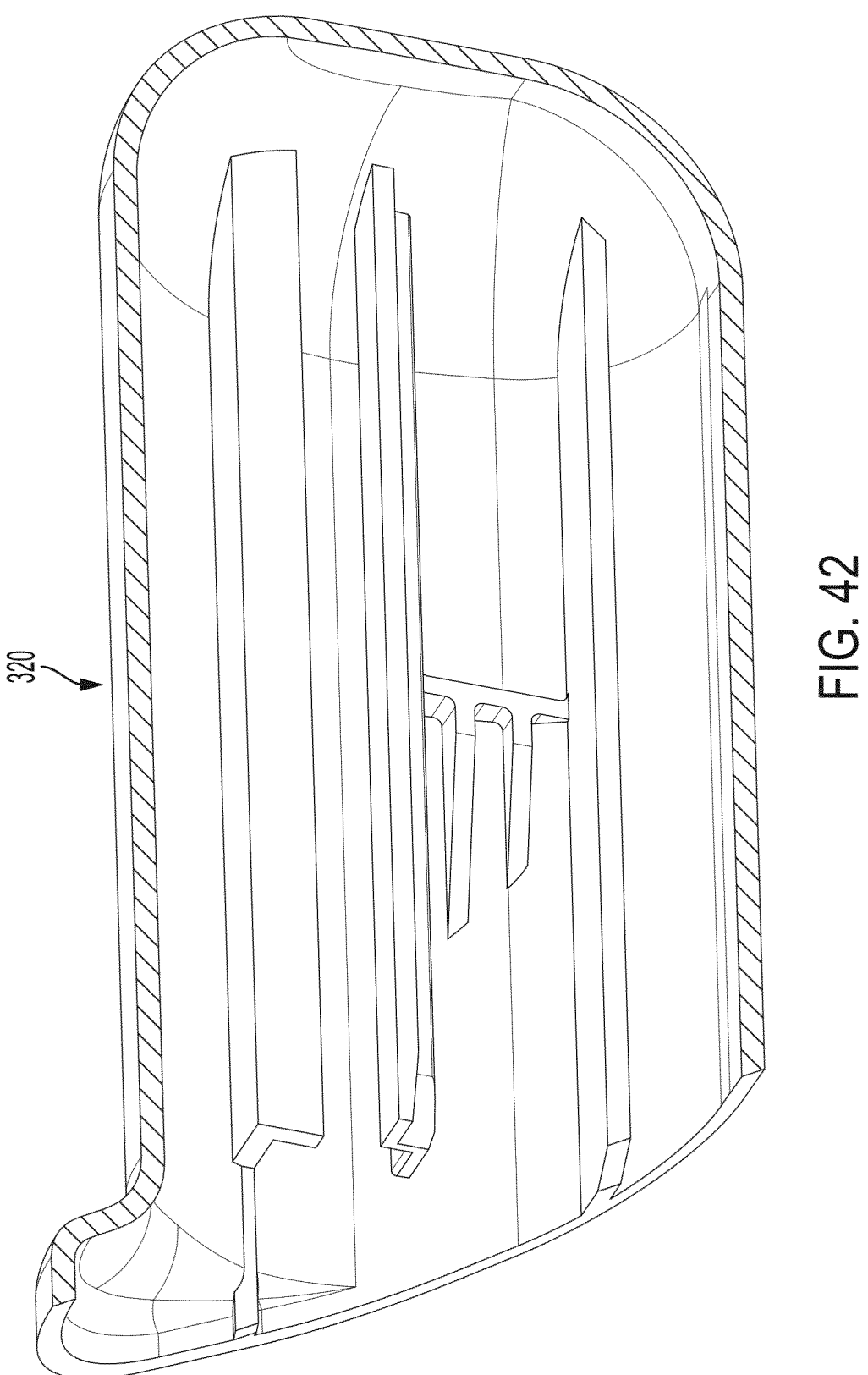

FIG. 42 is a cross-sectional view of an upper housing shell of the drug delivery device of FIG. 23.

Figure 43:
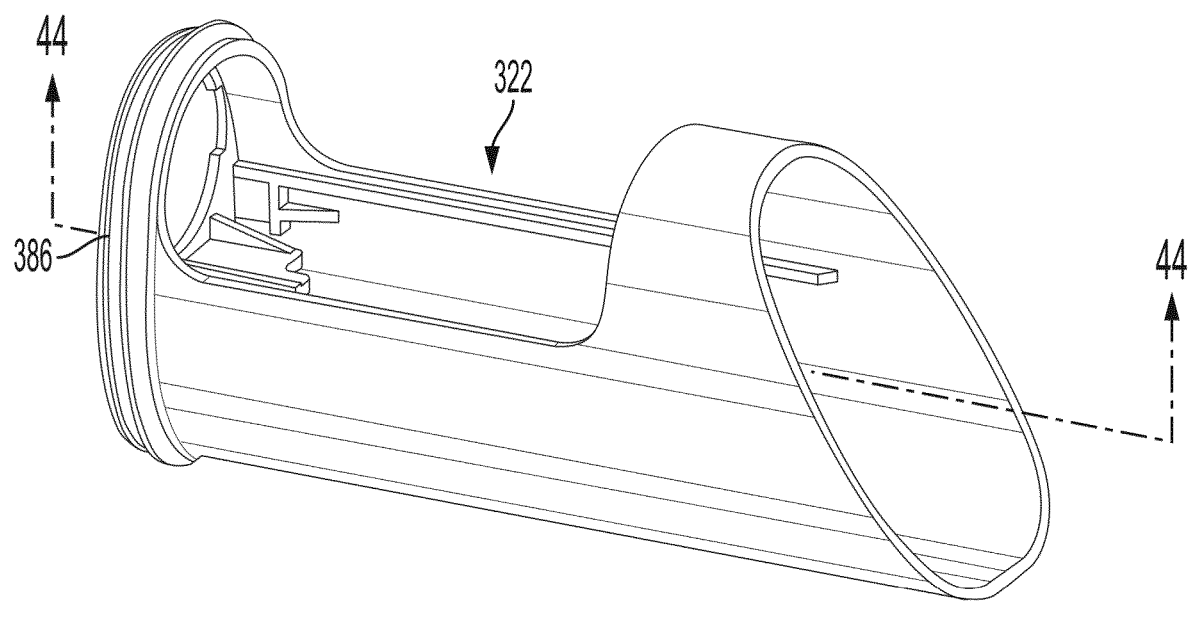

FIG. 43 is perspective view of a lower housing shell of the drug delivery device of FIG. 23.

Figure 44:
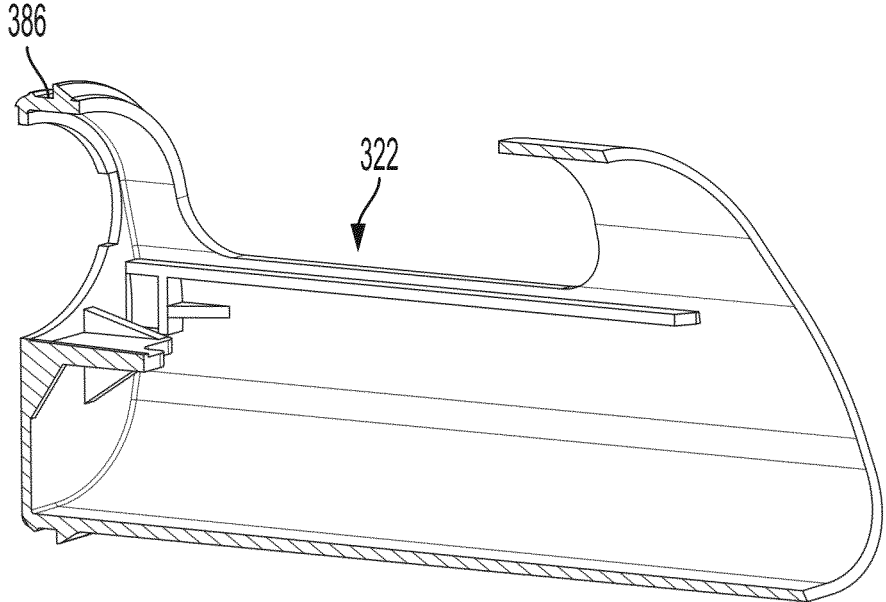

FIG. 44 is a cross-sectional view taken along line 44-44 in FIG. 43.

Figure 45:

FIG. 45 is a cross-sectional view of the drug delivery device of FIG. 23, showing an injection position of the device.

Figure 46:
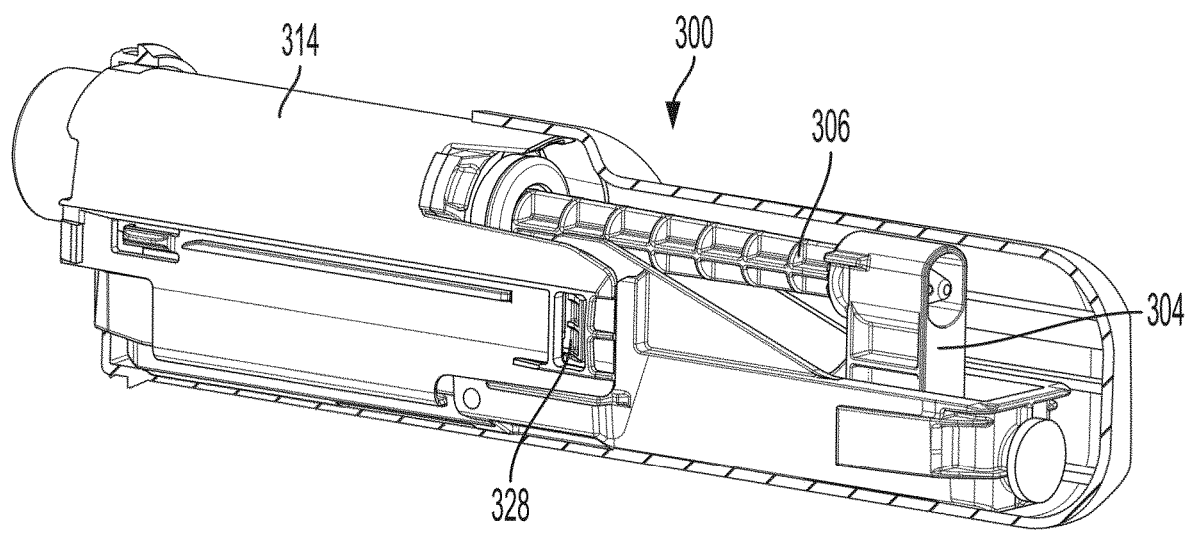

FIG. 46 is a partial cross-sectional view of the drug delivery system of FIG. 23.

Figure 47:
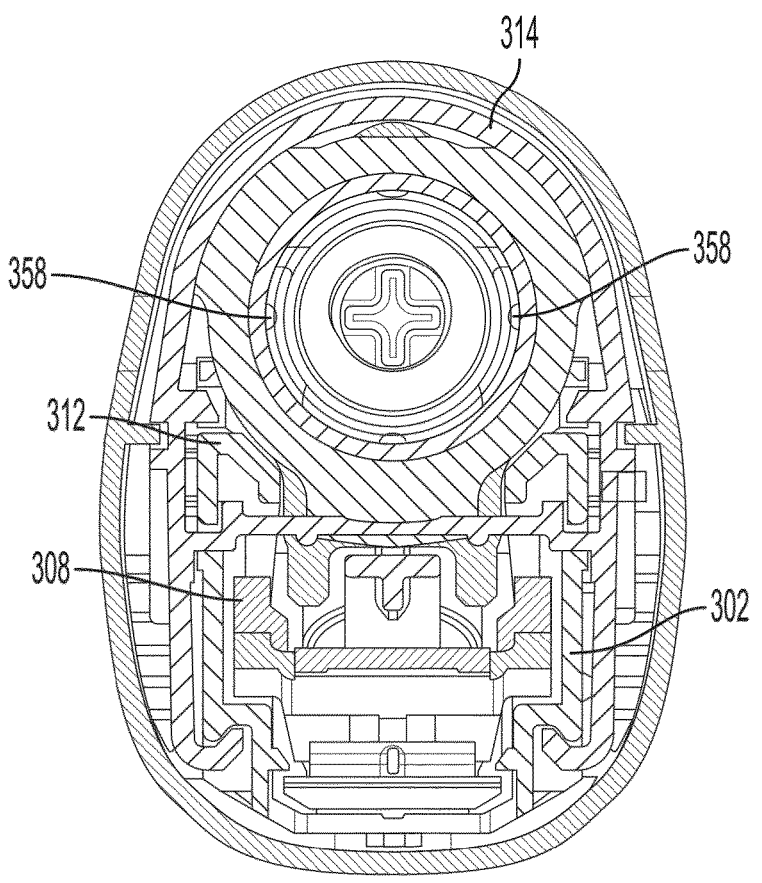

FIG. 47 is a cross-sectional view of the drug delivery system of FIG. 23.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1A-10 a drug delivery device 10 according to one aspect of the present invention includes a first subassembly 12, a second subassembly 14, and a syringe assembly 16. The first subassembly 12 includes a cap 18 having an outer portion 20, a needle cover 22, a syringe holder 24, a cassette body 26, and a lower housing shell 28. The second subassembly 14 includes a drive assembly 40, a motor body 42, a lever actuation member 44, and an upper housing shell 46. The syringe assembly 16 is received by the syringe holder 24 and includes a barrel 52, a stopper 54, a cannula 56, and a rigid needle shield (RNS) 58. The lower housing shell 28, the cassette body 26, and the upper housing shell 46 generally form a housing for receiving the various components of the device 10, although other suitable housing arrangements may be utilized. As discussed in more detail below, the first subassembly 12 and the second subassembly 14 are secured to each other during assembly by a locking clip 64, although other suitable arrangements may be utilized. The drug delivery device 10 may be an auto-injector, although the features described herein may be incorporated into other suitable drug delivery devices.

Figure 7:
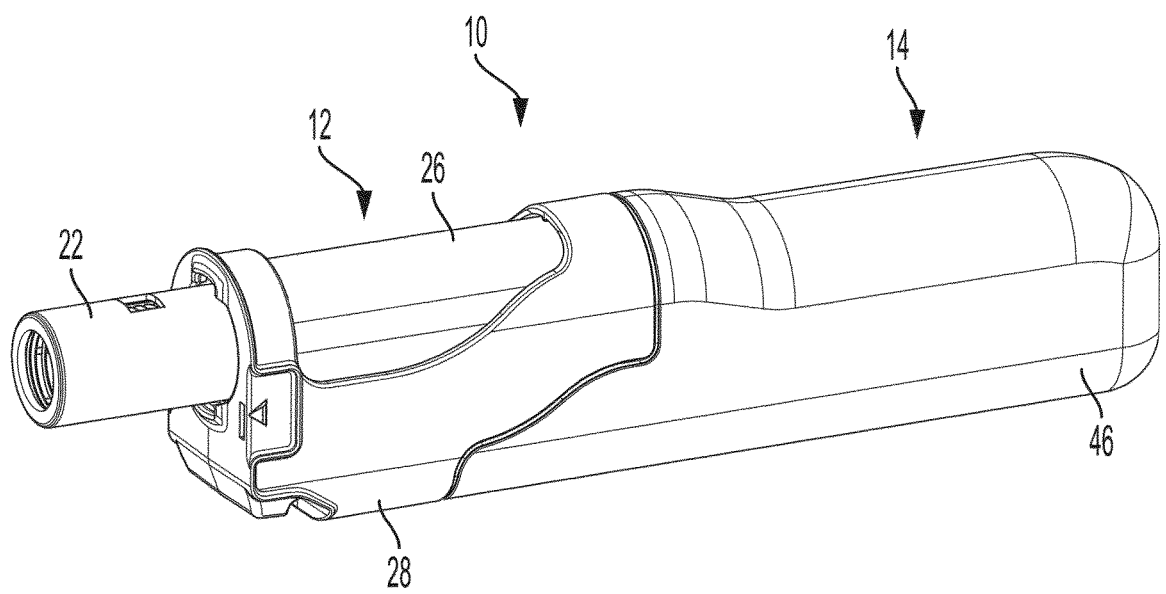
FIG. 7 is a perspective view of the drug delivery device of FIG. 1, showing a post-use position of the device.
Figure 8:
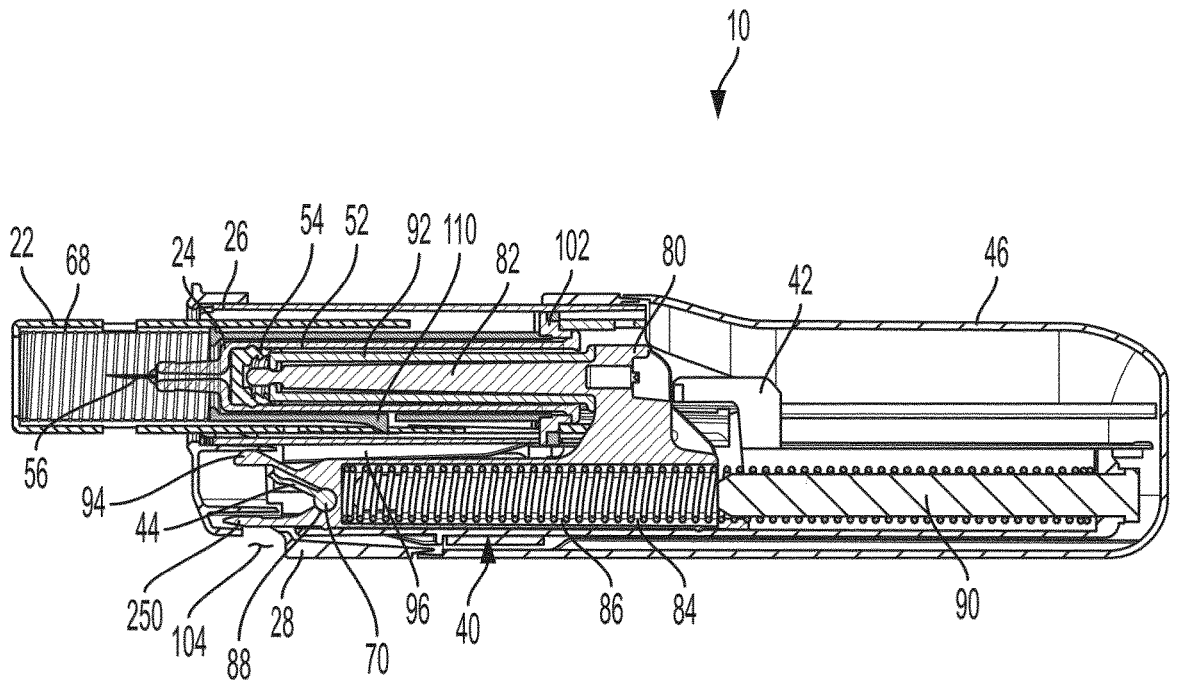
FIG. 8 is a cross-sectional view of the drug delivery device of FIG. 1, showing a post-use position of the device.
Figure 9:
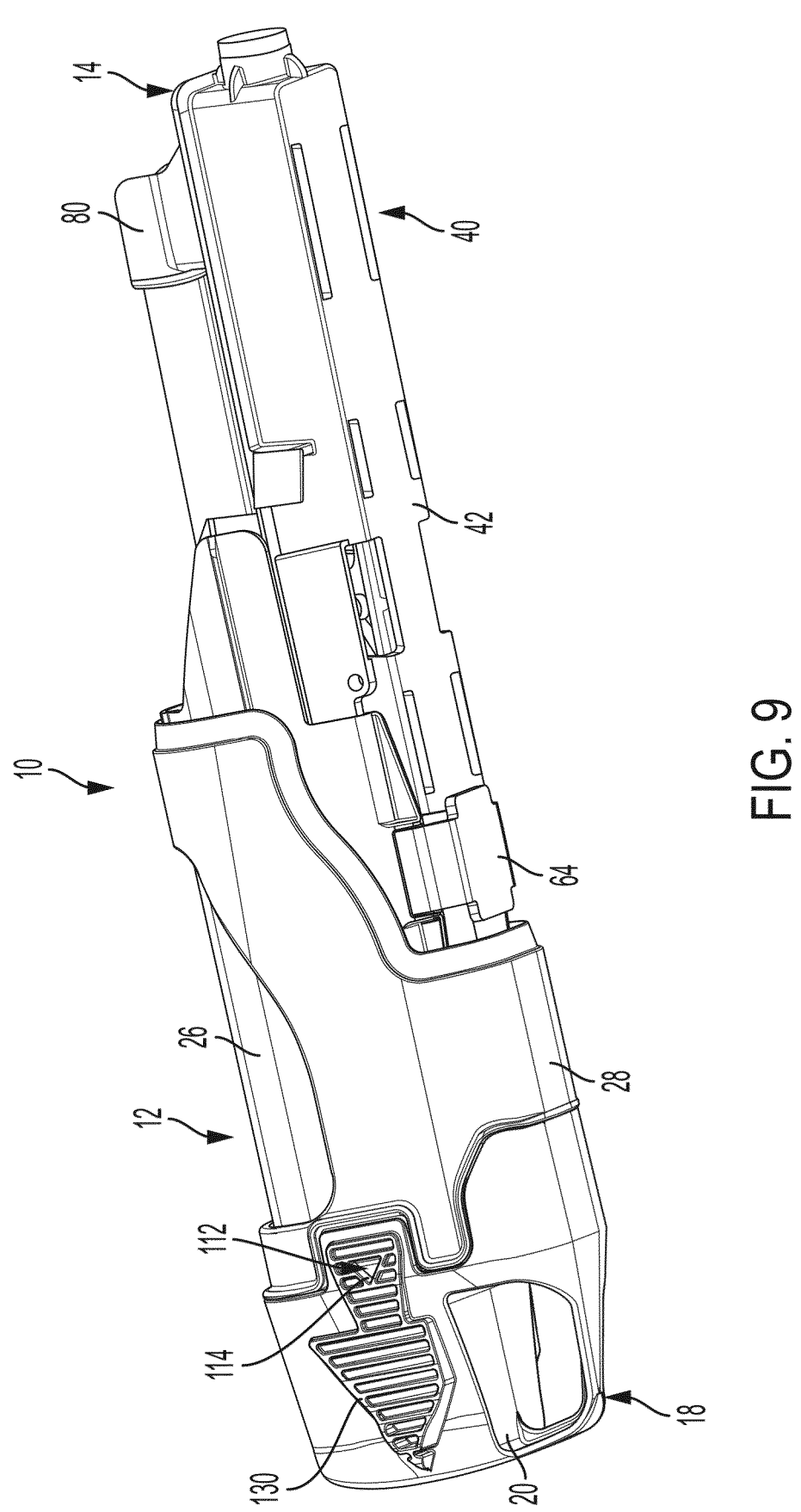
FIG. 9 is a perspective view of the drug delivery device of FIG. 1, showing a locking clip.
Figure 10:
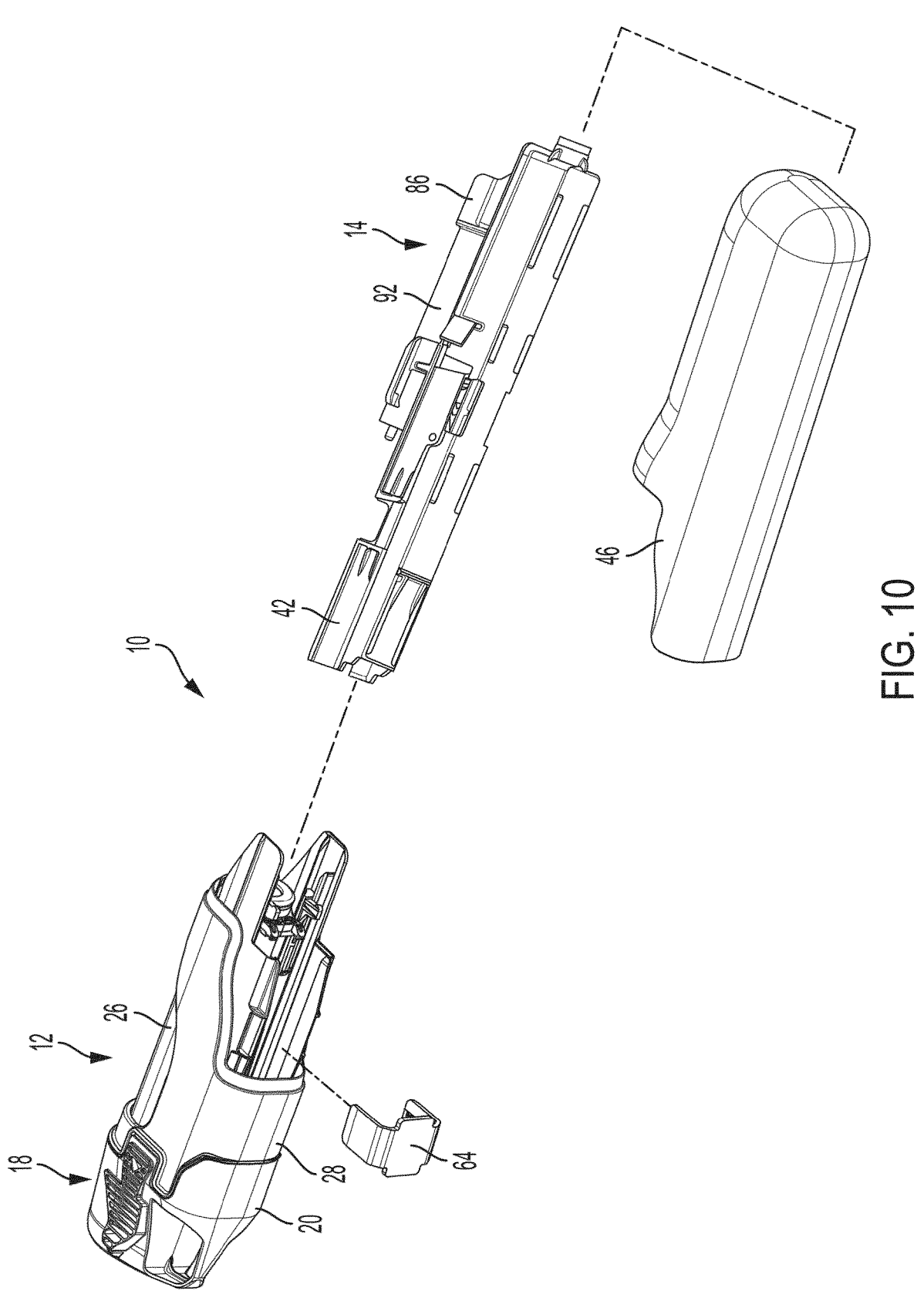
FIG. 10 is an exploded perspective view of the drug delivery device of FIG. 1, showing a locking clip.
Figure 11A:
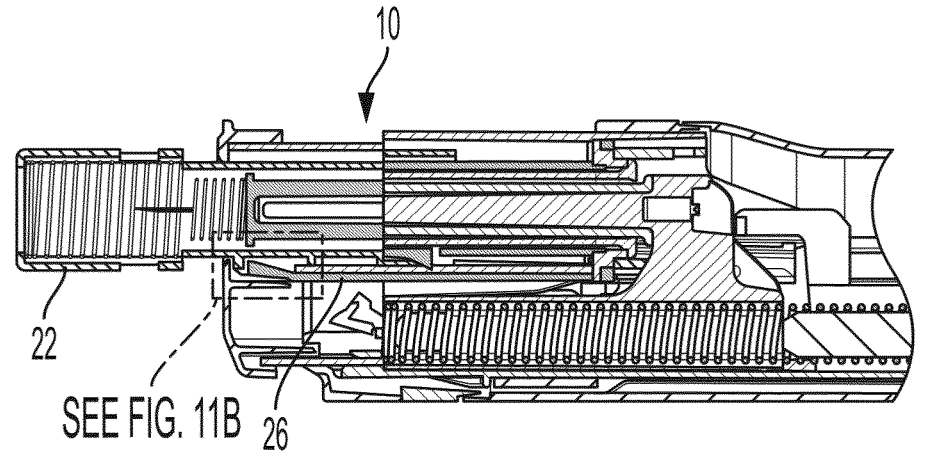
FIG. 11A is a partial cross-sectional view of the drug delivery device of FIG. 1, showing a lock arm of a cassette body.
Figure 11B:
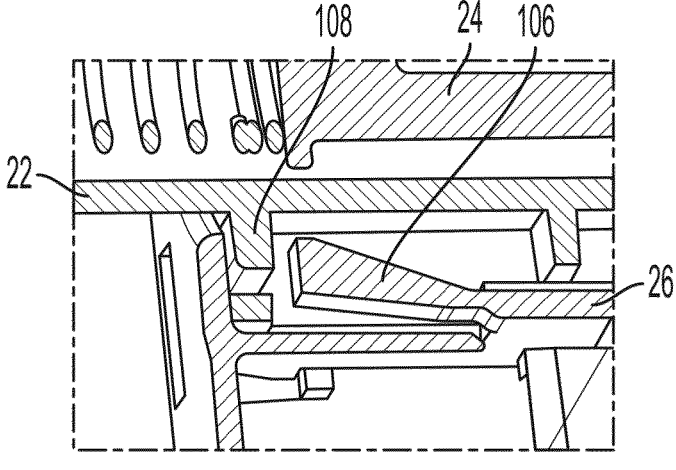
FIG. 11B is an enlarged cross-sectional view of the area indicated in FIG. 11A.

The drug delivery device 10 is configured to automatically deliver a dose of medicament from the syringe assembly 16 to a patient upon actuation of the device 10. More specifically, upon actuation of the drug delivery device 10, the drive assembly 40 is configured to engage the stopper 54 of the syringe assembly 16, displace the syringe assembly 16 such that the cannula 56 pierces the skin of the patient, and displace the stopper 54 within the barrel 52 of the syringe assembly 16 to deliver the medicament within the barrel 52. The drug delivery device 10 includes a storage position (FIGS. 1A and 2A), a pre-use position (FIGS. 1B and 2B), an actuation position (FIGS. 3 and 4), an injection position (FIGS. 5 and 6), and a post-use position (FIGS. 7 and 8). As discussed in more detail below, the needle cover 22 is configured to shield the cannula 56 of the syringe assembly 16 from the patient when the device 10 is in the pre-use and the post-use positions. In particular, the needle cover 22 is moveable between a pre-use position, an actuation position, and a post-use positon, with a spring 68 biasing the needle cover 22 towards the pre-use position and the post-use position. The spring 68 is positioned between the needle cover 22 and the syringe holder 24, although other suitable arrangements may be utilized. The lever actuation member 44 is moveable between a locked position where movement of the drive assembly 40 is prevented and a released position where movement of the drive assembly 40 is allowed. More specifically, the lever actuation member 44 is rotatable about a rotation axis 70 between the locked position and the released position. When the lever actuation member 44 is in the locked position, the lever actuation member 44 is engaged with the motor body 42 and the drive assembly 40 to prevent movement of the drive assembly 40. When the lever actuation member 44 is in the released position, the lever actuation member 44 is disengaged from the motor body 42 thereby allowing movement of the drive assembly 40 toward the syringe assembly 16. The rotation axis 70 of the lever actuation member 44 extends perpendicular to a longitudinal axis of the device 10, although other suitable arrangements may be utilized.

Referring again to FIGS. 1-10, the drive assembly 40 includes a plunger body 80 having a plunger rod portion 82 and a drive member 84. The drive member 84 is a compression spring received within a drive opening 86 defined by the plunger body 80, although other suitable drive members may be utilized, including, but not limited to, compressed gas, an electric motor, hydraulic pressure, other types of springs, etc. The drive member 84 engages the plunger body 80 and the motor body 42 and biases the plunger body 80 in a direction extending from the second subassembly 14 toward the first subassembly 12. The plunger body 80 defines a lever opening 88 that receives the lever actuation member 44 and defines the rotation axis 70 of the lever actuation member 44. The lever opening 88 is cylindrical and the portion of the plunger body 80 defining the rotation axis 70 is also cylindrical to allow for the smooth rotation of the lever actuation member 44 between the locked position and the released position. The lever actuation member 44 prevents movement of the plunger body 80 when the lever actuation member 44 is in the locked position through engagement of the lever actuation member 44 with the motor body 42. Upon rotation of the lever actuation member 44 from the locked position to the released position, the lever actuation member 44 is disengaged from the motor body 42 thereby allowing the drive member 84 to move the plunger body 80 and the plunger rod portion 82 toward the first subassembly 12. The plunger rod portion 82 and the drive member 84 are spaced from and parallel to each other and extend in a longitudinal direction of the device 10, which allows the device 10 to be more compact and to provide a stronger drive member to inject high viscosity drugs.

The drive assembly 40 further includes a spring guide member 90 secured to the upper housing shell 46 and received within the drive opening 86 of the plunger body 80. The drive member 84 is received by the spring guide member 90 such that the drive member 84 is positioned between the plunger body 80 and the spring guide member 90. The drive assembly 40 also includes a plunger rod cover 92 that receives the plunger rod portion 82 of the plunger body 80. The plunger rod cover 92 is configured to guide insertion of the plunger rod portion 82 into the barrel 52 of the syringe assembly 16 and engage the stopper 54 of the syringe assembly 16 to dispense the medicament from the barrel 52 of the syringe assembly 16. The plunger rod cover

92 and the plunger rod portion 82 may be formed integrally or formed as separate components.

The plunger body 80 of the drive assembly 40 also includes an audio indicator member 94 configured to provide an audible indication to a user when the device 10 transitions to the post-use position. As discussed in more detail below, the audio indicator member 94 is configured to engage one or more ribs 96 of the cassette body 26 when the device 10 is in the injection position thereby deflecting the audio indicator member 94. When the drug delivery device 10 transitions from the injection position to the post-use position, the audio indicator member 94 disengages from the rib(s) 96 of the cassette body 26 and contacts the lower housing shell 28 to provide an audible click, although the audio indicator member 94 could also contact other suitable portions of the device 10 to provide the audible indicator.

Figure 2A:
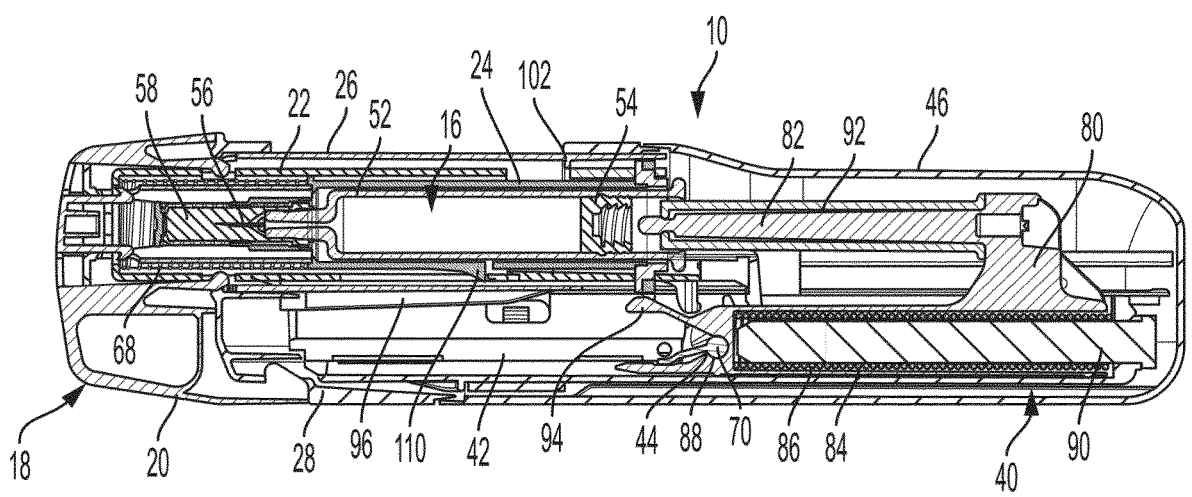
FIG. 2A is a cross-sectional view of the drug delivery device of FIG. 1, showing a storage position of the device.
Figure 2B:
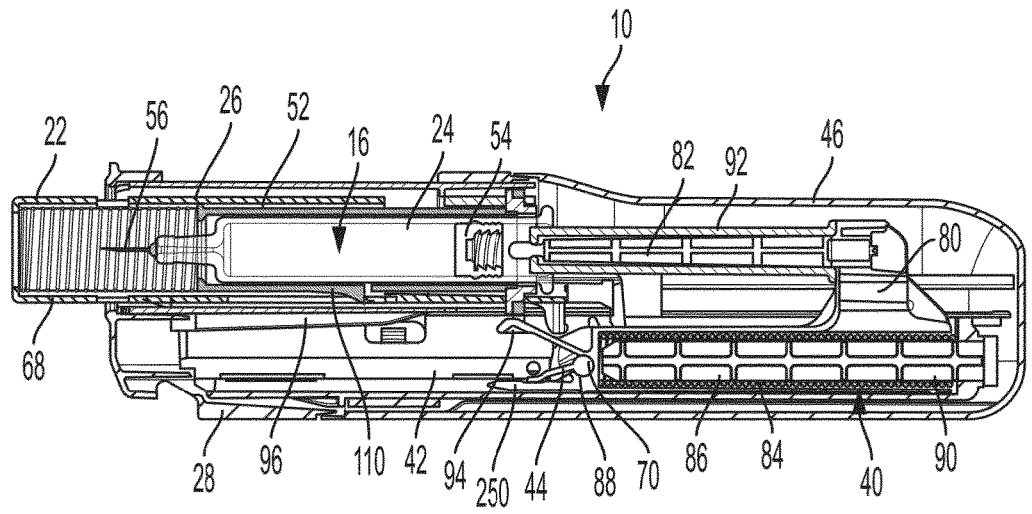
FIG. 2B is a cross-sectional view of the drug delivery device of FIG. 1, showing a pre-use position of the device.

Referring to FIGS. 1A-2B, in the storage position, the cap 18 is secured to the lower housing shell 28 and engaged with the needle cover 22. Movement of the needle cover 22 from the pre-use position to the actuation position causes engagement between the needle cover 22 and the lever actuation member 44 thereby actuating the drive assembly 40. In other words, the drive assembly 40 is actuated by movement of the needle cover 22 to the actuation position, which causes the lever actuation member 44 to rotate to the released position thereby releasing or allowing the drive assembly 40 to move into engagement with the stopper 54 and dispense medicament from the barrel 52. After removal of the cap 18 by grasping the outer portion 20, the needle cover 22 may be moved from the pre-use position to the actuation position by pressing the needle cover 22 against a skin surface of a patient and axially pressing the device 10 against the skin surface. As detailed below, the engagement between the cap 18 and the needle cover 22 prevents the needle cover 22 from moving into engagement with the lever actuation member 44. Accordingly, removal of the cap 18 from the device 10 allows for the actuation of the device 10. Removal of the cap 18 from the device 10, as shown in FIGS. 1B and 2B, also removes the RNS 58 from the syringe barrel 52 thereby exposing the cannula 56, which is still received within the needle cover 22 in the pre-use position of the device 10. The cap 18 may include one or more components received within the outer portion 20 to facilitate removal of the RNS 58.

Figure 3:
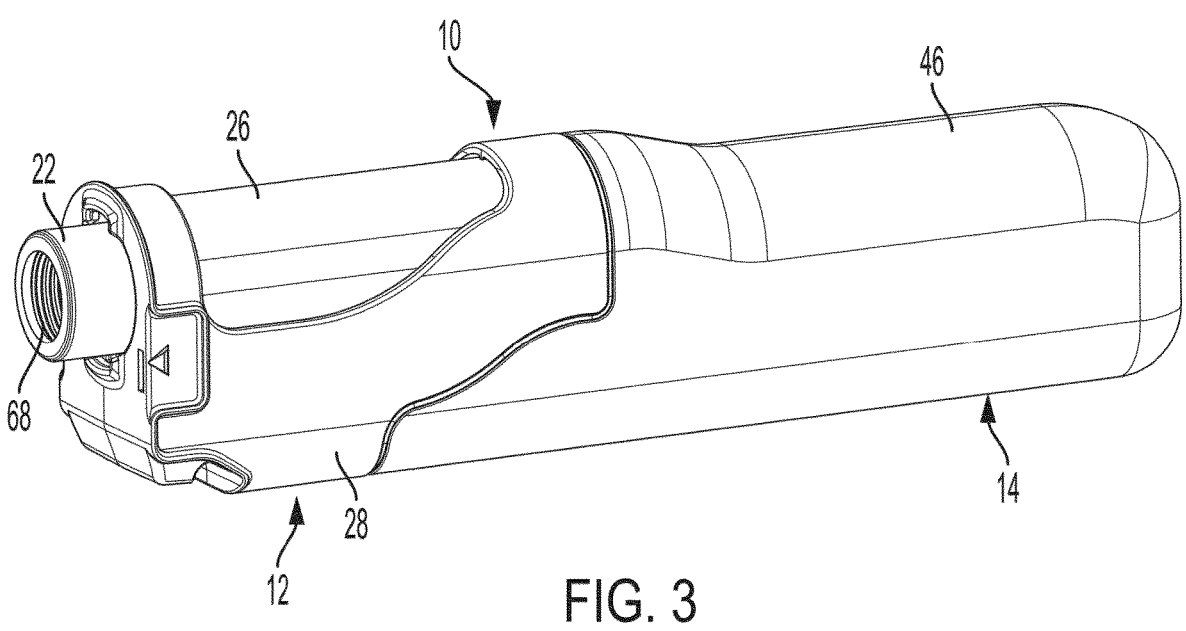
FIG. 3 is a perspective view of the drug delivery device of FIG. 1, showing an actuation position of the device.
Figure 4:
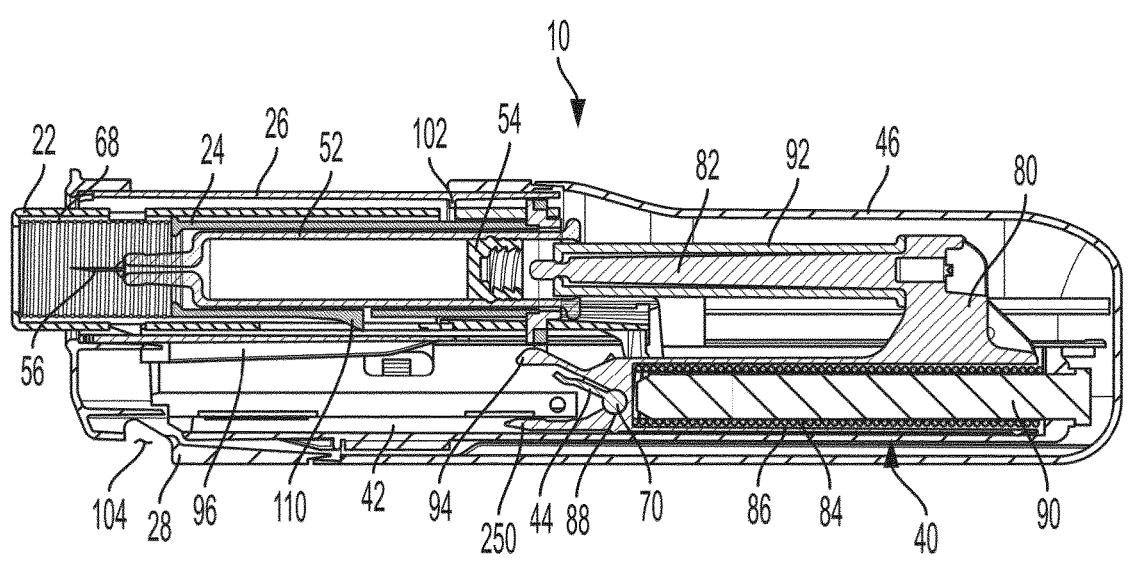
FIG. 4 is a cross-sectional view of the drug delivery device of FIG. 1, showing an actuation position of the device.

Referring to FIGS. 3 and 4, in the actuation position, the cap 18 is removed and the needle cover 22 is positioned in the actuation position by engaging a skin surface of a patient, which moves the needle cover 22 further within the device 10 toward the second subassembly 14. When the needle cover 22 has moved a sufficient distance within the device 10, a portion of the needle cover 22 engages the lever actuation member 44, which rotates the lever actuation member 44 about the rotation axis 70 from the locked position to the released position.

Figure 5:
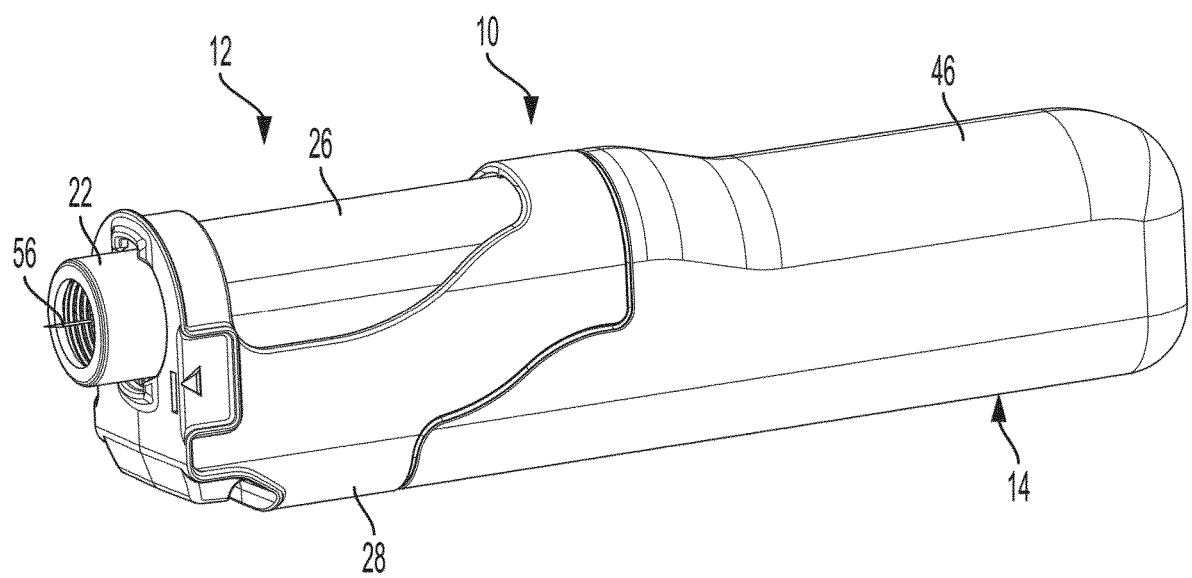
FIG. 5 is a perspective view of the drug delivery device of FIG. 1, showing an injection position of the device.
Figure 6:
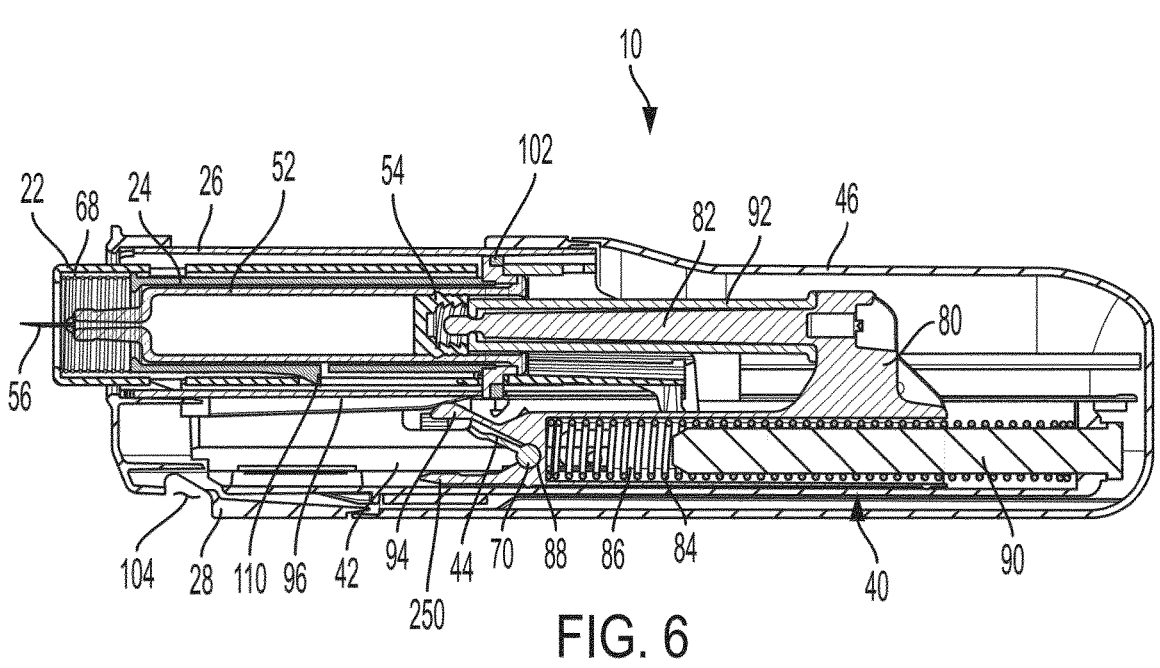
FIG. 6 is a cross-sectional view of the drug delivery device of FIG. 1, showing an injection position of the device.

Referring to FIGS. 5 and 6, in the injection position, the lever actuation member 44 is in the released position, which allows the plunger body 80 of the drive assembly 40 to move toward the first subassembly 12 such that the plunger body 80 or the plunger rod cover 92 engages the stopper 54 of the syringe assembly 16. Initial engagement of the drive assembly 40 with the syringe assembly 16 moves the syringe assembly 16 and the syringe holder 24 within the device 10 and relative to the cassette body 26 until the syringe holder 24 abuts a stop 102 defined by the cassette body 26. During this initial movement of the syringe assembly 16 and syringe holder 24 with the needle cover 22 pressed against a skin surface of a patient, the cannula 56 of the syringe assembly 16 extends beyond the needle cover 22 and pierces the skin surface of the patient. Further movement of the plunger body 80, which is driven by the drive member 84, moves the stopper 54 relative to the barrel 52 of the syringe assembly 16 to dispense medicament from the barrel 52 of the syringe assembly 16, through the cannula 56, and into the patient. The plunger body 80 will continue moving until the stopper 54 bottoms out on the barrel 52 of the syringe assembly 16. When the stopper 54 bottoms out, the audio indicator member 94 will disengage from the rib(s) 96 of the cassette body 26 and contact the lower housing shell 28 at approximately the same time to provide the audible indication to the patient that the dose of medicament has been delivered. In addition to the audible indication, the drug delivery device 10 provides one or more visual indicators to notify a patient of the status of the device 10. In particular, the cassette body 26 may be formed from transparent material to allow visual confirmation of movement of the stopper 54 and/or another visual indicator provided by the drive assembly 40, syringe holder 24, and/or syringe assembly 16. The lower housing shell 28 also defines an indicator opening 104, which provides visual indication that the plunger body 80 is in a final position and the dose of medicament has been delivered. The visual indicators may utilize contrasting colors, symbols, patterns, or any other suitable visual indicia to indicate the various statuses of the device 10.

Figure 12:
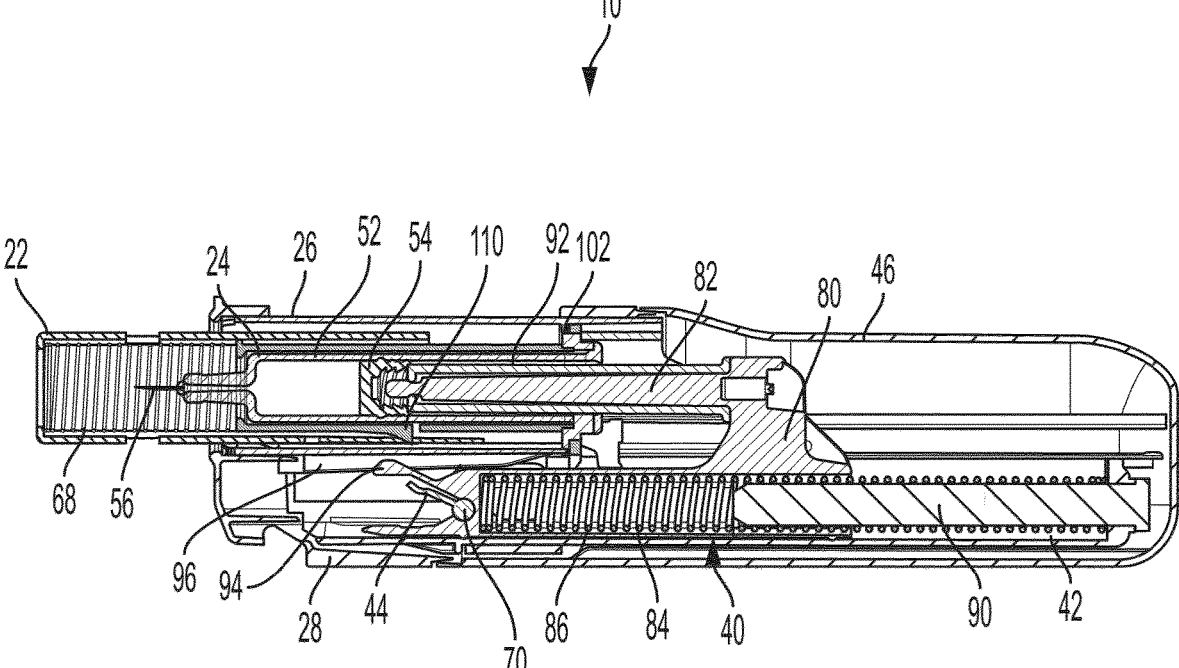
FIG. 12 is a cross-sectional view of the drug delivery device of FIG. 1, showing a post-use position of the device prior to full delivery of medicament.

Referring to FIGS. 7, 8, 11A, 11B, and 12, in the post-use position, the needle cover 22 extends to the post-use position to shield the cannula 56 when the needle cover 22 is removed from a skin surface of a patient. As shown more clearly in FIG. 11B, the cassette body 26 includes at least one lock arm 106 and the needle cover 22 includes at least one lock protrusion 108. The lock arm 106 of the cassette body 26 engages the lock protrusion 108 of the needle cover 22 to prevent any further use of the device 10 and exposing of the cannula 56 of the syringe assembly 16. During the transition of the device 10 from the injection position to the post-use position, the lock arm 106 of the cassette body 26 deflects to allow the lock protrusion 108 of the needle cover 22 to pass by the cassette body 26 with the lock arm 106 returning to its original position to prevent movement of the needle cover 22 back toward the pre-use and actuation positions. In the pre-use position of the needle cover 22, a portion of the needle cover 22 engages a cover stop 110 of the syringe holder 24 to limit axial movement of the needle cover 22 in a direction extending from the second subassembly 14 toward the first subassembly 12. The cover stop 110 also restricts axial movement of the needle cover 22 in the post-use position of the needle cover 22. After use of the device 10, the syringe holder 24 is displaced within the cassette body 26 relative to the needle cover 22, which allows the needle cover 22 to extend to the post-use position when a patient removes the needle cover 22 from a skin surface. As shown in FIG. 12, the needle cover 22 will move to the post-use position when the needle cover 22 is removed from a skin surface of a patient regardless of a position of the stopper 54 within the barrel 52 of the syringe assembly 16. Accordingly, if a patient removes the needle cover 22 from a skin surface after only a portion of the dose of medicament has been delivered, the needle cover 22 will still move to the post-use position and will prevent further use of the device 10.

Figure 13:
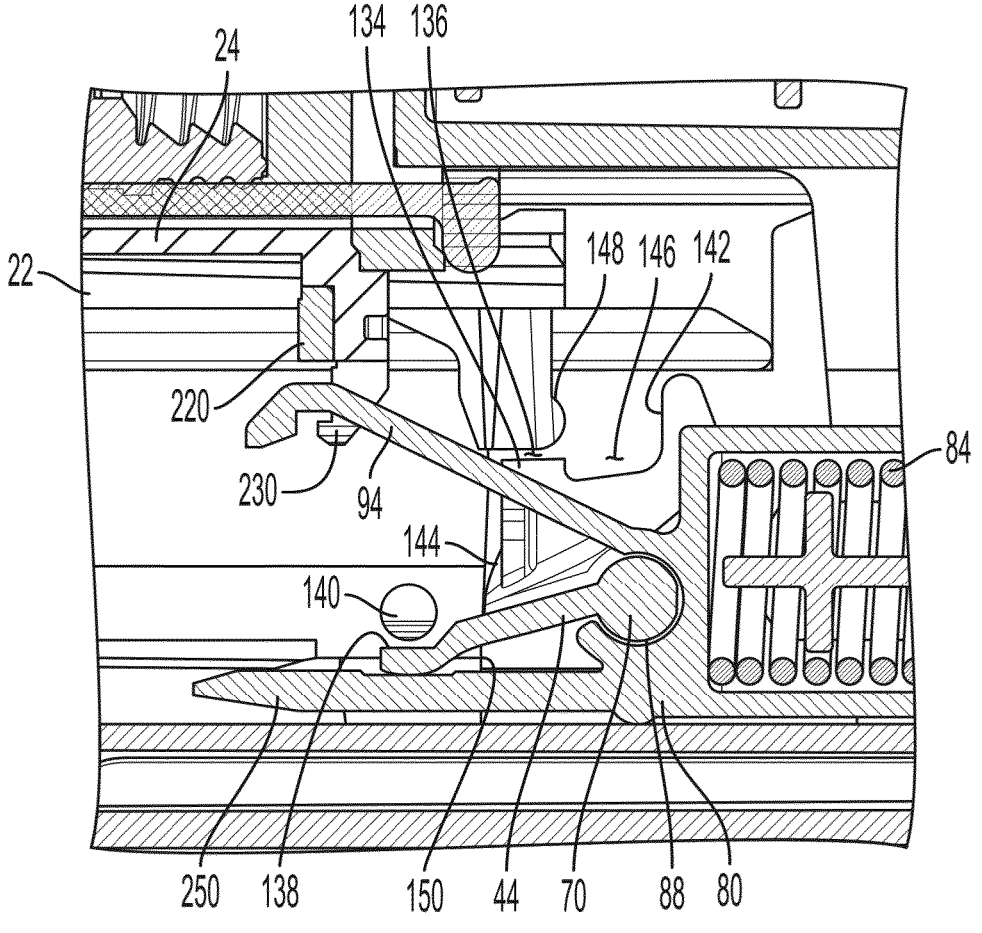
FIG. 13 is a partial cross-sectional view of the drug delivery device of FIG. 1, showing a pre-use position of the device.

Referring to FIGS. 1-21, as discussed above, engagement between the cap 18 and the needle cover 22 prevents the needle cover 22 from moving into engagement with the lever actuation member 44. The cannula 56 is positioned within the needle cover 22 when the needle cover 22 is in the pre-use position and the post-use position. The needle cover 22 is configured to actuate the drive assembly 40 when the needle cover 22 is in the actuation position. More specifically, as discussed above, the drive assembly 40 is actuated by movement of the needle cover 22 to the actuation position, which causes the lever actuation member 44 to rotate to the released position thereby releasing or allowing the drive assembly 40 to move into engagement with the stopper 54 and dispense medicament from the barrel 52. Removal of the cap 18 from the device 10 allows for the actuation of the device 10. The needle cover 22 prevents movement or rotation of the lever actuation member 44 from the locked position to the released position when the needle cover 22 is in the pre-use position. The lever actuation member 44 includes a body 132 having a restriction surface 134 configured to engage the needle cover 22 and restrict rotation of the lever actuation member 44 when the needle cover 22 is in the pre-use position. When the device 10 is in the storage position, if the device 10 is dropped or impacted to apply a force to the lever actuation member 44, the lever actuation member 44 is prevented from fully rotating to allow actuation of the drive assembly 40 due to the engagement between the restriction surface 134 of the lever actuation member 44 and the needle cover 22. As shown in FIG. 13, the restriction surface 134 is spaced from the needle shield 22 to form a gap 136 when the device 10 is in the storage and pre-use positions to prevent any increase in friction in the movement of the needle cover 22 while still preventing unintended actuation of the device 10.

The body 132 of the lever actuation member 44 also includes an assembly surface 138 configured to engage a locking pin (not shown) received by a pin opening 140 defined by the motor body 42. Prior to assembly, the second subassembly 14 may include a locking pin that extends through the pin opening 140, which prevents rotation of the lever actuation member 44 and unintentional actuation of the drive assembly 40 during assembly of the device 10. The body 132 of the lever actuation member 44 also includes a needle cover contact surface 142, a motor body contact surface 144, and defines a recessed area 146.

Referring to FIGS. 13-19B and 21, the needle cover contact surface 142 of the lever actuation member 44 engages a lever contact portion 148 of the needle cover 22 when the needle cover 22 is moved to the actuation position thereby rotating the lever actuation member 44 from the locked position to the released position. The lever contact portion 148 is preferably located on a lever actuation arm 152 of the needle cover 22, located at a distal end or at a proximal end of the needle cover 22. The lever actuation arm 152 preferably protrudes radially from a proximal end of the needle cover 22. The lever contact portion 148 of the needle cover 22 defines a cylindrical surface 202 and the needle cover contact surface 142 of the lever actuation member 44 defines a planar surface 204. The engagement between the cylindrical surface 202 of the lever contact portion 148 and the planar surface 204 of the needle cover contact surface 142 reduces the amount of effort required to rotate the lever actuation member 44. The motor body contact surface 144 of the lever actuation member 44 engages a stop surface 150 of the motor body 42 when the lever actuation member 44 is in the locked position, which prevents movement of the plunger body 80. When the lever actuation member 44 rotates from the locked position to the released position, the motor body contact surface 144 disengages from the stop surface 150 of the motor body 42, which allows the drive member 84 to move the plunger body 80. The stop surface 150 of the motor body 42 defines a planar surface 210 and the motor body contact surface 144 of the lever actuation member 44 defines a cylindrical surface 212. The engagement between the planar surface 210 of the stop surface 150 and the cylindrical surface 212 of the motor body contact surface 144 reduces the amount of effort required to rotate the lever actuation member 44.

Referring to FIGS. 13-18, the recessed area 146 of the lever actuation member 44 provides clearance for the lever contact portion 148 of the needle cover 22 to allow for rotation of the lever actuation member 44 from the locked position to the released position, which ensures the actuation of the device 10. The position of the restriction surface 134 of the lever actuation member 44 overlaps in an axial direction of the device 10 with the position of the lever contact portion 148 of the needle cover 22 when the needle cover 22 is in the pre-use position and until the needle cover 22 has fully moved to the actuation position, which prevents unintentional actuation of the device 10 as discussed above. When the needle cover 22 is fully moved to the actuation position, the lever contact portion 148 of the needle cover 22 no longer overlaps with the position of the restriction surface 134 of the lever actuation member 44 and, instead, overlaps with the position of the recessed area 146 in a direction extending in an axial direction of the device 10 and engages the needle cover contact surface 142 to rotate the lever actuation member 44 as described above.

Referring to FIGS. 1-8 and 20, the syringe holder 24 further includes a securing ring 220 configured to receive and secure the syringe assembly 16. In particular, the securing ring 220 is positioned at one end of the syringe holder 24 with the barrel 52 of the syringe assembly 16 extending through the securing ring 220. A flange of the barrel 52 abuts the securing ring 220. The securing ring 220 is formed from a thermoplastic elastomer, although other suitable materials may be utilized.

Referring to FIGS. 13 and 20, the audio indicator member 94 is also configured to restrict movement of the syringe holder 24 when the plunger body 80 is in the pre-use position. As discussed above, the lever actuation member 44 prevents movement of the plunger body 80 and the syringe holder 24 is moveable relative to the cassette body 26. The audio indicator member 94 engages at least one arm 230 of the syringe holder 24 to prevent movement of the syringe holder 24 during movement of the device 10 in the pre-use position or during removal of the cap 18. The arm(s) 230 extend radially outward from the syringe holder 24 with a portion of the audio indicator member 94 positioned between the arm(s) 230 of the syringe holder 24 such that movement of the syringe holder 24 in a direction extending from the second subassembly 14 toward the first subassembly 12 causes at least one of the arm(s) 230 to engage the audio indicator member 94 to restrict any further movement of the syringe holder 24.

Referring to FIGS. 4, 6, 8, and 13, as mentioned above, the device 10 also includes a visual indicator member 250 configured to provide a visual indication of a transition of the plunger body 80 from the injection position (FIG. 6) to the post-use position (FIG. 8). The visual indicator member 250 is visible via the indicator opening 104 defined by the lower housing shell 28. The visual indicator 250 member is formed integrally with the plunger body 80 and spaced from the audio indicator member 94, although other suitable configurations may be utilized. As noted above, the visual indicator member 220 may utilize contrasting colors, symbols, patterns, or any other suitable visual indicia to indicate the various statuses of the device. The lever opening 88 of the plunger body 80 is positioned between the audio indicator member 94 and the visual indicator member 250, although other suitable configurations may be utilized.

Referring to FIG. 22, the cassette body 26 defines at least one guiding groove 240 extending along a longitudinal axis of the cassette body 26. The guide groove(s) 240 receives the arm(s) 230 of the needle cover 22 and guides the movement of the needle cover 22 within the device 10 and relative to the cassette body 22 between the pre-use position, the actuation position, and the post-use position. The guide groove(s) 240 fixes the transverse position of the needle cover 22 to ensure that the lever contact portion 148 of the needle cover 22 stays aligned with the needle cover contact surface 142 of the lever actuation member 44 thereby ensuring the lever contact portion 148 engages the needle cover contact surface 142 when the needle cover 22 moves to the actuation position.

Figure 14:
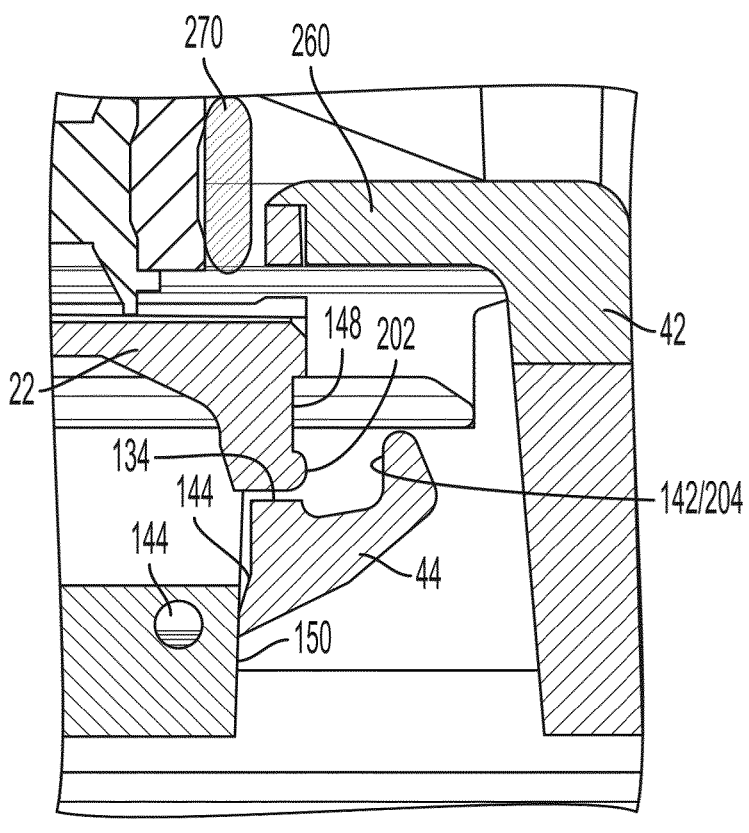
FIG. 14 is a partial cross-sectional view of the drug delivery device of FIG. 1, showing a pre-use position of the device.
Figure 15:
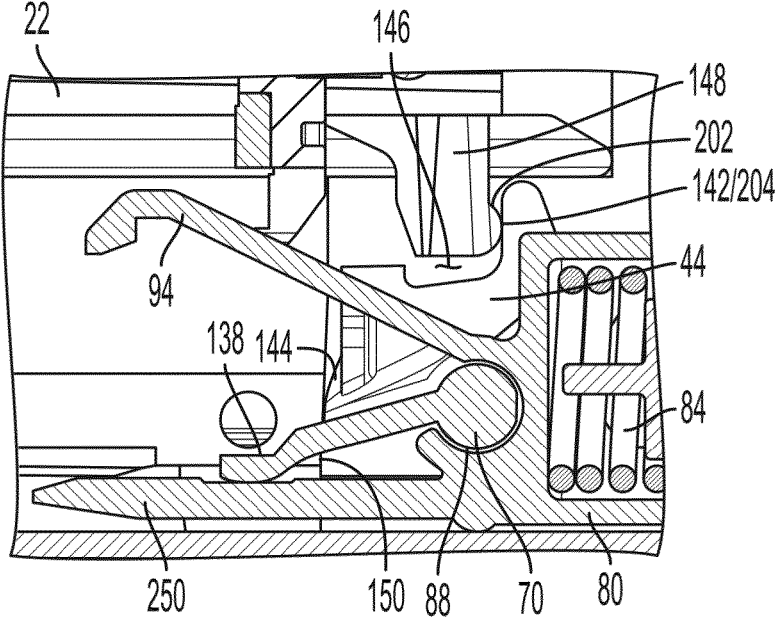
FIG. 15 is a partial cross-sectional view of the drug delivery device of FIG. 1, showing a transition from a pre-use position to an actuation position of the device.
Figure 16:
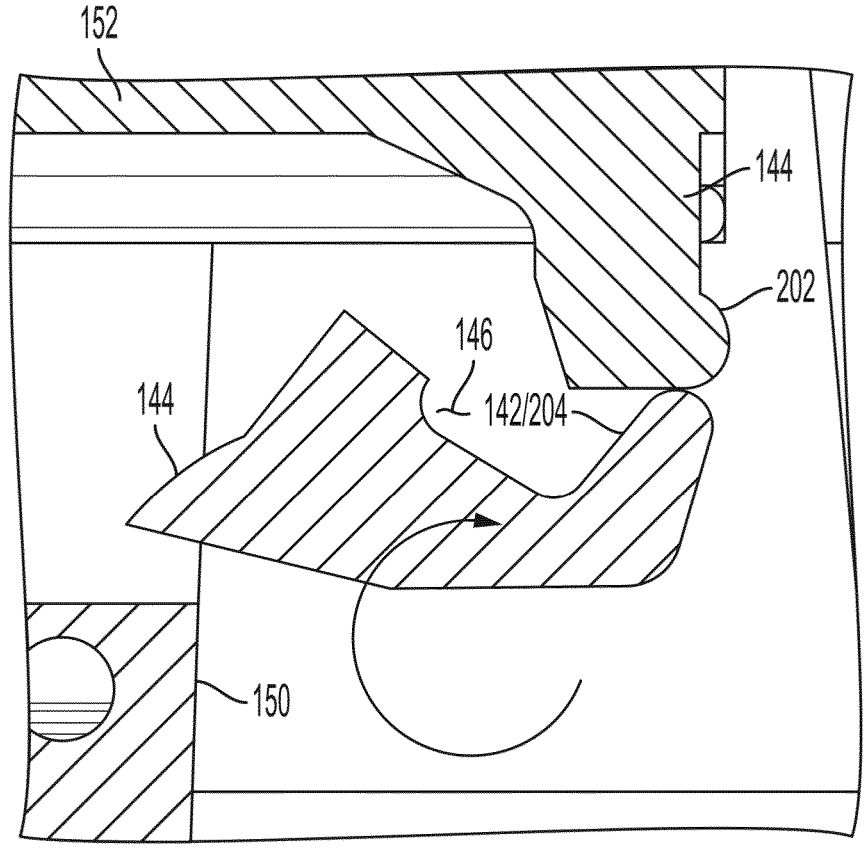
FIG. 16 is a partial cross-sectional view of the drug delivery device of FIG. 1, showing an actuation position of the device.

Referring to FIGS. 14, 20, and 21, the motor body 42 includes arm 260 extending from the motor body 42. As shown in FIG. 14, the arm 260 is configured to engage a flange 270 of the barrel 52 of the syringe assembly 16. Accordingly, the barrel 52 of the syringe assembly 16 constrained at one end by the syringe holder 24 and at the other end by the arm 260 of the motor body 42 thereby securing the syringe assembly 16 within the syringe holder 24. The motor body 42 includes a pair of arms 260 on each side of the motor body 42, although the motor body 42 may include one or more arms 260. The arms 260 are L-shaped, although other suitable shapes and configurations may be utilized.

Referring to FIGS. 23-47, a drug delivery device 300 according to a further aspect of the present invention is shown. The drug delivery device 300 is similar to the drug delivery device 10 shown in FIGS. 1A-22, with certain differences discussed below in detail. The drug delivery device 300 includes, among other components, a motor body 302, a plunger body 304, a plunger rod portion 306, a lever actuation member 308, a syringe holder 310, a needle cover 312, a cassette body 314, a cap 316, a retainer 318, an upper housing shell 320, and a lower housing shell 322.

Referring to FIGS. 23-26, the motor body 302 is similar and functions similarly to the motor body 42 of FIGS. 1A-22, but further includes a longitudinal groove 324, reinforcing rib(s) 326, and cassette clip(s) 328. The longitudinal groove 324 is configured to receive a molding split line of the plunger body 304 to ensure smooth sliding between the motor body 302 and the plunger body 304. The reinforcing rib(s) 326 provide additional support for the pair of arms 260 of the motor body 302. The cassette clip(s) 328 is received by an opening(s) 330 defined by the cassette body 314 to secure the motor body 302 to the cassette body 314, which is discussed in more detail below. The cassette clip(s) 328 include an angled face 332 and a planar face 334, which is configured to allow insertion of the cassette clip(s) 328 into the opening(s) 330 of the cassette body 314, but prevent the easy removal of the cassette clip(s) 328 once inserted into the opening(s) 330 of the cassette body 314. A bottom surface 336 of the motor body 302 includes chamfered portions 338 to aid assembly of the device 300.

Referring to FIGS. 24 and 27-30, the plunger body 304 is formed separately from the plunger rod portion 306 rather than being formed integrally. Further, the device 300 does not include the plunger rod cover 92. The plunger body 304 defines an opening 340 that receives a plunger rod clip 342 of the plunger rod portion 306. The plunger rod clip 342 is barb-shaped and configured to be inserted into the opening 340 of the plunger body 304, but not easily removed from the opening 340, although other suitable shapes and configurations may be utilized. The plunger rod clip 342 defines a central opening 344, which allows the plunger rod clip 342 to compress as the plunger rod clip 342 is inserted into the opening 340 of the plunger body 304 and expand to its original shape once received within the plunger body 304. The plunger rod portion 306 includes a plunger body stop(s) 346 and a biasing member 348. The plunger body stop(s) 346, which may be one or more projections, contact the plunger body 304 when the plunger rod clip 342 is inserted into the opening 340 of the plunger body 304. The biasing member 348 engages the plunger body 304 during insertion of the plunger rod clip 342 into the opening 340 of the plunger body 304 and biases the plunger rod portion 306 toward the plunger body 304. The biasing member 348 provides additional leeway for insertion of the plunger rod clip 342 into the opening 340 of the plunger body 304 while ensuring there is no gap between the plunger body 304 and the plunger rod portion 306 after assembly. The biasing member 348 of the plunger rod portion 306 is annular, although other suitable shapes and configurations may be utilized.

The plunger rod portion 306 further includes a stopper interface 350 that is received by the stopper 54. The stopper interface 350 is a cruciform projection, although other suitable shapes and configurations may be utilized. The plunger rod portion 306 has a conical external shape configured to reduce stress on the syringe assembly 16, although other suitable shapes may be utilized. The plunger body 304 includes a lever rib 352 extending into the lever opening 88 of the plunger body 304. The lever rib 352 is configured to be received by the lever actuation member 308, as discussed in more detail below.

Referring to FIGS. 31 and 32, the lever actuation member 308 is similar to and functions similarly to the lever actuation member 44 described above and shown in FIGS. 1A-22. The lever actuation member 308, however, defines a groove 354 at the rotation axis 70 that receives the lever rib 352 of the plunger body 304. The engagement between the groove 354 and the lever rib 352 prevents relative lateral movement between the plunger body 304 and the lever actuation member 308. The needle cover contact surface 142 of the lever actuation member 308 includes a larger surface compared to the needle cover contact surface 142 of the lever actuation member 44 of FIGS. 1A-22.

Referring to FIGS. 33 and 34, the syringe holder 310 is similar to and functions similarly to the syringe holder 24 of FIGS. 1A-22. The syringe holder 310, however, further includes a plurality of ribs 356 extending circumferentially around the syringe holder 310. The plurality of ribs engage the spring 68. The securing ring 220 of the syringe holder 310 further includes a plurality of projections 358 that extend radially inward. The plurality of projections 358 engage the syringe assembly 16 to remove any gap between the outer surface of the syringe assembly 16 and the syringe holder 310. The plurality of projections 358 are elastomeric and may compress when the syringe assembly 16 is received within the syringe holder 310.

Referring to FIGS. 35 and 36, the needle cover 312 is similar to and functions similarly to the needle cover 22 of FIGS. 1A-22. The needle cover 312 includes a spring rib 360 which engages the spring 68 to hold the spring 68 between the needle cover 312 and the syringe holder 310. The needle cover 312 also includes a cassette rib(s) 362 to guide movement of the needle cover 312 relative to the cassette body 314.

Referring to FIGS. 37, 38, 46, and 47, the cassette body 314 is similar to and functions similarly to the cassette body 26 of FIGS. 1A-22. As discussed above, the cassette body 314 includes the opening(s) 330 that receive the cassette clip(s) 328 of the motor body 302. The cassette body 314 includes a needle cover clip(s) 364 that engage clip surface (s) 366 of the needle cover 312. The clip surface(s) 366 of the needle cover 312 are planar, although other suitable shapes and configurations may be utilized. The needle cover clip(s) 364 are configured to restrict the axial movement of the needle cover 312 relative to the cassette body 314. The cassette body 314 further includes motor body rib(s) 368 and upper housing shell rib(s) 370, which are configured to engage corresponding portions of the motor body 302 and the upper housing shell 320 to aid in the assembly of the device 300. The cassette body 314 also includes syringe holder stop(s) 372, which are configured to engage portions of the syringe holder 310 to limit the axial movement of the syringe holder 310 relative to the cassette body 314. Although not shown in FIG. 46, the locking clip 64 may also be utilized with the drug delivery device 300.

Referring to FIGS. 39-44, the cap 316 is similar to and functions similarly to the cap 18 described above and shown in FIGS. 1A-22. The cap 316 includes a protrusion(s) 374 that is received by a cap opening(s) 376 defined by the needle cover 312, which is positioned 90 degrees relative to the position of those elements of the cap 18 of FIGS. 1A-22. The protrusion(s) 374 of the cap 316 is configured to engage the needle cover 312 upon movement of the needle cover 312 from the pre-use position to the actuation position. For instance, with the device 300 in the storage position with the cap 316 secured to the lower housing shell 322, if the device is dropped or impacted to apply a force to the needle cover 312, the lever actuation member 308, and/or other component, the protrusion(s) 374 restricts movement of the needle cover 312, which prevents any unintended actuation of the device 300. The cap 316 further includes a retainer clip(s) 378 and a rib(s) 380 for engaging a wing(s) 382 of the retainer 318. The retainer clip(s) 378 and the rib(s) 380 secure the retainer 318 to the cap 316 and prevent any movement or wobbling of the retainer 318 relative to the cap 316. The retainer 318 is configured to remove the RNS 58 when the cap 316 is removed from the lower housing shell 322. The cap 316 includes a lower housing shell clip(s) 384 for engaging the lower housing shell 322 to secure the cap 316 to the lower housing shell 322. The upper housing shell 320 and the lower housing shell 322 are similar and function similarly to the upper housing shell 46 and the lower housing shell 28 discussed above and shown in FIGS. 1A-22. The lower housing shell 322, however, has a cap interface 386 to receive the lower housing shell clip(s) 384 of the cap 316.

Referring to FIG. 45, the drug delivery device 300 is shown in an injection position. The injection depth of the cannula 56 is determined by contact between the syringe holder 310 and the cassette body 314 at point X and contact between the needle cover 312 and the syringe holder 310 at point Y.

Referring to FIG. 45, the drug delivery device 300 includes an audio indicator member 388, which is similar to and functions similarly to the audio indicator member 94 described above and shown in FIGS. 1A-22. In the same manner as the audio indicator member 94, which is described above, the audio indicator member 388 of the drug delivery device 300 is configured to provide an audible indication to a user when the device 300 transition to the post-use position. The audio indicator member 388 is configured to engage rib(s) 390 of the cassette body 314 when the device 300 is in the injection position thereby deflecting the audio indicator member 388. The audio indicator member 388 disengages from the rib(s) 390 of the cassette body 314 and contacts the lower housing shell 322 to provide an audible click when the drug delivery device 300 transition from the injection position to the post-use position. However, a distal end 392 of the rib(s) 390 of the cassette body 314 is angled rearward toward the upper housing shell 320, which beneficially provides a louder audible click compared to the arranged of the rib(s) 96 of the cassette body 26 discussed above in connection with FIGS. 1A-22.

In one aspect or embodiment, an angle Z of the distal end 392 of the rib(s) 390 of the cassette body 314 relative to a plane extending perpendicularly to a longitudinal axis of the device 300 is greater than 5 degrees. In one aspect or embodiment, the angle Z of the distal end 392 of the rib(s) 390 is greater than 10 degrees. In one aspect or embodiment, the angle Z of the distal end 392 is 25 degrees.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A drug delivery device comprising:
a housing;
a syringe assembly comprising a barrel, a stopper, and a cannula,
at least a portion of the syringe assembly positioned within the housing;
a drive assembly associated with a motor body receiving at least a portion of the drive assembly, the drive assembly configured to move the stopper within the barrel upon actuation of the drive assembly, at least a portion of the drive assembly positioned within the housing;
a lever actuation member moveable between a locked position where the actuation of the drive assembly is prevented and a released position where the actuation of the drive assembly is allowed; and
a needle cover having a pre-use position where the cannula is positioned within the needle cover, an actuation position where the drive assembly is actuated, and a post-use position where the cannula is positioned within the needle cover, the needle cover configured to contact and engage the lever actuation member and move the lever actuation member to the released position when the needle cover is moved into the actuation position,
wherein the needle cover contacts the lever actuation member and prevents the movement of the lever actuation member from the locked position to the released position when the needle cover is in the pre-use position,
wherein the lever actuation member is rotatable about a rotation axis of the lever actuation member extending perpendicular to a longitudinal axis of the device, between the locked position and the released position,
wherein the lever actuation member comprises a restriction surface configured to engage the needle cover and restrict the rotation of the lever actuation member in a direction of the released position when the needle cover is in the pre-use position, and an assembly surface, distal to the rotation axis of the lever actuation member, configured to engage a locking pin that extends through a pin opening in the motor body in a perpendicular direction with respect to the longitudinal axis of the device and parallel to the rotation axis of the lever actuation member to prevent rotation of the lever actuation member and unintentional actuation of the drive assembly during assembly of the device, and
wherein the drive assembly is actuated by the movement of the needle cover to the actuation position.

2. The drug delivery device of claim 1, further comprising a syringe holder moveable relative to the housing between a first position and a second position, the syringe assembly received by the syringe holder.

3. The drug delivery device of claim 2, wherein the syringe holder is configured to move from the first position to the second position when the needle cover is in the actuation position, a portion of the cannula of the syringe assembly extending outside of the needle cover when the syringe holder is in the second position and when the needle cover is in the actuation position.

4. The drug delivery device of claim 3, wherein a portion of the needle cover engages a cover stop of the syringe holder to restrict axial movement of the needle cover in at least one direction when the needle cover is in the pre-use position.

5. The drug delivery device of claim 1, wherein the drive assembly comprises a plunger body having a plunger rod portion and a drive member, the drive member is configured to move the plunger body within the housing.

6. The drug delivery device of claim 5, wherein a longitudinal axis of the plunger rod portion is spaced from and parallel to a longitudinal axis of the drive member.

7. The drug delivery device of claim 5, wherein the drive member comprises a compression spring.

8. The drug delivery device of claim 1, wherein the restriction surface of the lever actuation member is spaced from the needle cover to form a gap when the needle cover is in the pre-use position.

9. The drug delivery device of claim 1, wherein the needle cover comprises a lever contact portion and the lever actuation member comprises a needle cover contact surface, the lever contact portion of the needle cover is configured to engage the needle cover contact surface of the lever actuation member and rotate the lever actuation member about the rotation axis from the locked position to the released position when the needle cover is in the actuation position.

10. The drug delivery device of claim 9, wherein the lever actuation member defines a recessed area configured to receive a portion of the lever contact portion of the needle cover when the needle cover is in the actuation position.

11. The drug delivery device of claim 9, wherein the lever contact portion of the needle cover defines a cylindrical surface and the needle cover contact surface of the lever actuation member defines a planar surface.

12. The drug delivery device of claim 1, wherein the motor body comprises a stop surface and the lever actuation member comprises a motor body contact surface, wherein the motor body contact surface of the lever actuation member is engaged with the stop surface of the motor body when the lever actuation member is in the locked position and is disengaged from the stop surface of the motor body when the lever actuation member is in the released position.

13. The drug delivery device of claim 12, wherein the stop surface of the motor body defines a planar surface and the motor body contact surface of the lever actuation member defines a cylindrical surface.

* * * * *

18